(12) United States Patent
Faraji Rad et al.

(10) Patent No.: US 10,850,082 B2
(45) Date of Patent: Dec. 1, 2020

(54) MICROFLUIDIC DEVICES AND FABRICATION

(71) Applicants: NewSouth Innovations Pty Limited, Sydney, New South Wales (AU); The University of Birmingham, Birmingham, W.M. (GB)

(72) Inventors: Zahra Faraji Rad, Sydney (AU); Robert Ernest Nordon, Sydney (AU); Graham James Davies, Sydney (AU); Carl John Anthony, Birmingham (GB); Philip Prewett, Birmingham (GB)

(73) Assignees: NewSouth Innovations Pty Limited, Sydney (AU); The University of Birmingham, Birmingham (GB)

( * ) Notice: Subject to any disclaimer, the term of this patent is extended or adjusted under 35 U.S.C. 154(b) by 620 days.

(21) Appl. No.: 15/508,519

(22) PCT Filed: Sep. 3, 2015

(86) PCT No.: PCT/AU2015/050518
§ 371 (c)(1),
(2) Date: Mar. 3, 2017

(87) PCT Pub. No.: WO2016/033652
PCT Pub. Date: Mar. 10, 2016

(65) Prior Publication Data
US 2017/0274196 A1      Sep. 28, 2017

(30) Foreign Application Priority Data

Sep. 3, 2014    (AU) .............................. 2014903523

(51) Int. Cl.
*A61M 37/00*    (2006.01)
*B29C 33/38*    (2006.01)
(Continued)

(52) U.S. Cl.
CPC ... *A61M 37/0015* (2013.01); *A61B 5/150022* (2013.01); *A61B 5/150282* (2013.01);
(Continued)

(58) Field of Classification Search
CPC ............ A61M 37/0015; B81C 1/00111; B81C 99/0085; B29C 33/3885; B29C 51/082; A61B 17/205
See application file for complete search history.

(56) References Cited

U.S. PATENT DOCUMENTS 9,289,925 B2    3/2016    Ferguson et al.
9,302,903 B2 *  4/2016    Park ..................... A61B 5/1411
(Continued)

FOREIGN PATENT DOCUMENTS

CN    102458559 A    5/2012
CN    102836936 A    12/2012
(Continued)

OTHER PUBLICATIONS

International Search Report pertaining to PCT/AU2015/050518, filed Sep. 3, 2015 (6 pages).
(Continued)

*Primary Examiner* — Manuel A Mendez
(74) *Attorney, Agent, or Firm* — Myers Bigel, P.A.

(57) ABSTRACT

Methods for mass production of new microfluidic devices are described. The microfluidic devices may include an array of micro-needles with open channels in fluid communication with multiple reservoirs located within a substrate that supports the micro-needles. The micro-needles are configured so as to sufficiently penetrate the skin in order to collect or sample bodily fluids and transfer the fluids to the reservoirs. The micro-needles may also deliver medicaments into or below the skin.

16 Claims, 27 Drawing Sheets

(51) Int. Cl.
*B01L 3/00* (2006.01)
*B29C 33/42* (2006.01)
*B29C 33/40* (2006.01)
*A61B 5/15* (2006.01)
*B29C 39/00* (2006.01)
*B29C 43/02* (2006.01)
*B29C 39/26* (2006.01)
*B81B 1/00* (2006.01)
*B81C 1/00* (2006.01)
*B29C 59/02* (2006.01)
*B29L 31/00* (2006.01)
*B29K 101/12* (2006.01)

(52) U.S. Cl.
CPC .. *A61B 5/150419* (2013.01); *A61B 5/150984* (2013.01); *B01L 3/502707* (2013.01); *B01L 3/502715* (2013.01); *B29C 33/3857* (2013.01); *B29C 33/3878* (2013.01); *B29C 33/40* (2013.01); *B29C 33/405* (2013.01); *B29C 33/42* (2013.01); *B29C 39/003* (2013.01); *B29C 39/26* (2013.01); *B29C 43/021* (2013.01); *B81B 1/006* (2013.01); *B81C 1/00111* (2013.01); *A61M 2037/003* (2013.01); *A61M 2037/0038* (2013.01); *A61M 2037/0053* (2013.01); *B01L 2200/12* (2013.01); *B01L 2300/0672* (2013.01); *B01L 2300/0861* (2013.01); *B01L 2300/12* (2013.01); *B01L 2300/161* (2013.01); *B29C 2043/025* (2013.01); *B29C 2059/023* (2013.01); *B29K 2101/12* (2013.01); *B29K 2821/00* (2013.01); *B29L 2031/756* (2013.01); *B29L 2031/7544* (2013.01); *B81B 2201/055* (2013.01); *B81B 2203/0361* (2013.01)

(56) References Cited

U.S. PATENT DOCUMENTS

| | | | |
|---|---|---|---|
| 10,413,711 | B2 | 9/2019 | Luttge et al. |
| 2002/0099356 | A1* | 7/2002 | Unger ............... A61N 1/30 604/501 |
| 2003/0045837 | A1 | 3/2003 | Delmore et al. |
| 2006/0084942 | A1* | 4/2006 | Kim ............... A61K 9/0021 604/890.1 |
| 2008/0015494 | A1* | 1/2008 | Santini, Jr. ......... A61M 5/1409 604/65 |
| 2015/0030642 | A1 | 1/2015 | Wu et al. |
| 2016/0067176 | A1* | 3/2016 | Ding ............... A61M 37/0015 604/46 |

FOREIGN PATENT DOCUMENTS

| | | | |
|---|---|---|---|
| CN | 103301092 | A | 9/2013 |
| CN | 103568160 | A | 2/2014 |
| CN | 103691054 | A | 4/2014 |
| JP | 2007260351 | A | 10/2007 |
| JP | 2008237673 | A | 10/2008 |
| JP | 2008265001 | A | 11/2008 |
| WO | 2009146911 | A2 | 12/2009 |
| WO | 2011/121427 | A2 | 10/2011 |
| WO | 2012168807 | A2 | 12/2012 |
| WO | 2013170171 | A1 | 11/2013 |

OTHER PUBLICATIONS

Written Opinion pertaining to PCT/AU2015/050518, filed Sep. 3, 2015 (8 pages).
Extended European Search Report (EESR) pertaining to EP Application No. 15837736.6 dated Aug. 2, 2018.
Gittard et al., "Two-photon polymerization of microneedles for transdermal drug delivery", Expert Opinion on Drug Delivery, Mar. 7, 2010, pp. 513-533, vol. 7, No. 4.
Kim et al., "Microneedles for drug and vaccine delivery", Advanced Drug Delivery Reviews, Nov. 1, 2012, pp. 1547-1568, vol. 64, No. 14.
Roxhed et al., "Penetration-Enhanced Ultrasharp Microneedles and Prediction on Skin Interaction for Efficient Transdermal Drug Delivery", Journal of Microelectromechanical Systems, Dec. 1, 2007, pp. 1429-1440, vol. 16, No. 6.
English translation of Chinese Search Report issued with Office Action dated Apr. 3, 2020, Application No. 201580057081.1, Application date Sep. 3, 2015, 3 pgs.
Communication pursuant to Article 94(3) EPC, EP Application No. 15837736.6, Jul. 16, 2020, 10 pages.
Nu Skin: "Skin Anatomy and Physiology", Jul. 09, 2020, Retrieved from the Internet: URL: https://www.nuskin.com/en_ZA/corporate/company/scienceiskin_care_scienceiskin_anatomy_andphysiology.html [retrieved on Jul. 09, 2020], 5 pages.
Gill et al.: "Effect of microneedle design on pain in human subjects", Aug. 06, 2010, Retrieved from the Internet: URL: https://www_ncbi_nlm_nih.govipmc/articles/PMC2917250/ [retrieved on Jul. 09, 2020], 19 pages.

* cited by examiner

2610

MICROFLUIDIC DEVICES AND FABRICATION

BACKGROUND OF THE INVENTION

Field of the Invention

This invention relates to the field of microfluidic devices. Specifically, the invention relates to a micro-needle for penetrating an epidermal layer and delivering or sampling fluids to or from a human or animal body. The invention further relates to a patch or micro-fluidic device comprising an array of microneedles for communicating bodily fluids, and a method of manufacturing the micro-needle and the patch or a micro-fluidic device.

Description of the Art

Drawing fluids from the body and introducing fluids and medicaments into the body have long been used as a practice for treating and diagnosing medical conditions, both in animals and human beings. Typically these procedures are done with a hypodermic needle or similar catheter arrangement.

There are many drawbacks associated with hypodermic needles, least of all the painful experience of being injected, which ranges from uncomfortable to extremely painful. A fear of needles can cause complications: a biological reaction such as peripheral vasoconstriction or a physical reaction making a subject restless or worse combative.

There is a desire to reduce the pain felt by a subject when communicating fluids with (in or out of) the body. However, a more serious drawback is the level of operator skill required to carry out procedures using hypodermic needles. Securing and ensuring the availability or people with the requisite level of training can place resource burdens and budget constraints on a medical practice. In a worst case scenario, a subject could be prevented from receiving a necessary treatment.

For some subjects, particularly infants, children and the aged, there can be a range of venous access complications associated with using hypodermic needles for example fragility of veins, poor vein visibility and palpability, low blood pressure, volume depletion, peripheral vasoconstriction, scarred or damaged veins and rolling veins causing difficulties to puncture.

Subtractive manufacturing methods such as machine tooling or etching have physical limitations that restrict their application to the manufacture of micro-needle and microfluidic medical devices. These physical limitations mean that some but not all the geometric features required for skin penetration and fluid transport within the micro-fluidic device may be economically mass produced. Chemical wet etching (Yun, S.-S., A. Jae-Yong, M. Seung-Hwan, and L. Jong-Hyun. *In-plane microneedle chip fabricated by crystalline wet etching of (110) silicon wafer*. in *Solid-State Sensors, Actuators and Microsystems Conference, 2009. TRANSDUCERS 2009. International*. 2009), deep reactive ion etching (Wilke, N., A. Mulcahy, S. R. Ye, and A. Morrissey, *Process optimization and characterization of silicon microneedles fabricated by wet etch technology*. Microelectronics Journal, 2005. 36(7): p. 650-656), surface/bulk micromachining (Izumi, H. and S. Aoyagi, *Novel fabrication method for long silicon microneedles with three-dimensional sharp tips and complicated shank shapes by isotropic dry etching*. IEEJ Transactions on Electrical and Electronic Engineering, 2007. 2(3): p. 328-334), laser drilling (Parker, E. R., M. P. Rao, K. L. Turner, C. D. Meinhart, and N. C. MacDonald, *Bulk Micromachined Titanium Microneedles*. Microelectromechanical Systems, Journal of, 2007. 16(2): p. 289-295) and drawing lithography techniques (Lee, K. and H. Jung, *Drawing lithography for microneedles: A review of fundamentals and biomedical applications*. Biomaterials, 2012. 33(30): p. 7309-7326; and Xiang, Z. L., H. Wang, A. Pant, G. Pastorin, and C. Lee, *Development of vertical SU-8 microneedles for transdermal drug delivery by double drawing lithography technology*. Biomicrofluidics, 2013. 7(6)) lack the precision to accurately manufacture three dimensional micro-fluidic devices from theoretical computer assisted drawings. For example isotropic and anisotropic (Bosch process) Deep Reactive Ion Etching (DRIE) processes may be used to etch high density nanoprojection arrays (Jenkins, D., S. Corrie, C. Flaim, and M. Kendall, *High density and high aspect ratio solid micro-nanoprojection arrays for targeted skin vaccine delivery and specific antibody extraction*. RSC Advances, 2012. 2(8): p. 3490-3495) but without microfluidic channels for transfer of fluid between the dermis and the micro medical device for collection and/or analysis. In addition DRIE is not suited to manufacture longer microneedles (>300 micro-metres height/length) with side channels (Faraji Rad, Z., *Microneedles Fabrication for Subcutaneous Fluid Sampling and Drug Delivery*, in *Graduate School of Biomedical Engineering*. 2015, University of New South Wales: Sydney. p. 181). Micro-needles of length less than 300 micro-metres may not be suitable for collecting bodily fluids due to insufficient depth of penetration.

For the widespread cheap application of micro-fluidic devices for diagnostic or therapeutic purposes, highly economic mass production techniques are required. In particular the cost per unit needs to be low enough for widespread use in third world countries.

None of these prior art methods or devices provides an entirely satisfactory solution to the provision of a microfluidic device with a micro-needle, nor to the ease of mass production of the micro-fluidic device.

Any reference herein to known prior art does not, unless the contrary indication appears, constitute an admission that such prior art is commonly known by those skilled in the art to which the invention relates, at the priority date of this application.

SUMMARY OF THE INVENTION

The present invention aims to provide an alternative micro-fluidic and micro-needle arrangement and a method for mass production which overcomes or ameliorates the disadvantages of the prior art, or at least provides a useful choice In one embodiment, the invention provides a method of replicating a microfluidic device, including the steps of: providing a master die of the microfluidic device; casting a mould of the master die; separating the mould from the master die; isothermally heating the mould with a thermoplastic material to a sufficient temperature; maintaining the sufficient temperature; compressing the thermoplastic material into the mould to a sufficient pressure; maintaining the sufficient pressure; reducing the compressing and the heating simultaneously over approximately the same time period; and separating the mould from the replica microfluidic device.

In another form, the invention provides an improved method of producing replica microfluidic devices of a thermoplastic material by embossing from a master die of a microfluidic device, wherein the improvement comprises the steps of: isothermally heating the mould with a thermoplastic material to a sufficient temperature; maintaining the sufficient temperature; compressing the thermoplastic material into the mould to a sufficient pressure; maintaining the sufficient pressure; and reducing the compressing and the isothermal heating simultaneously over approximately the same time period.

The compressing step may continue until a bulk flow of the thermoplastic material across and into the mould is completed.

The isothermally heating step may include a surface flow of the thermoplastic material into the mould.

The sufficient temperature may cause a surface flow across the mould by the thermoplastic material, prior to the compressing step to the sufficient pressure.

The sufficient temperature may be selected from the approximate range of 30° to 55° C. greater than a glass transition temperature for the thermoplastic material. Alternatively, the sufficient temperature may be selected from the approximate range of 55° to 65° C. greater than a glass transition temperature for the thermoplastic material.

The sufficient temperature may be approximately 160° C. for a cyclic olefin polymer.

The maintaining of the sufficient temperature may be within approximately +/−1° C. or within approximately +/−0.1° C.

The maintaining of the sufficient pressure may be within approximately +/−1 kPa or is within approximately +/−0.1 kPa.

The thermoplastic material may be at least one of: a medical grade plastic, a cyclic olefin polymer, Zeonor® 1060R, polytetrafluoroethylene (PTFE), polyetheretherketone (PEEK), polystyrene, and polycarbonate.

The method wherein a mould material may be at least one of: a silicone elastomer, elastomeric, silicone rubber, a polydimethylsiloxane (PDMS), SYLGARD 184 Silicone Elastomer, polyurethane elastomeric alloys, rubber and latex.

The microfluidic device may include an array of micro-needles.

The microfluidic device may include at least one reservoir in fluid communication with at least one open channel of the plurality of micro-needles.

The microfluidic device may include an upright blade with a plurality of channels extending down the blade to at least one reservoir.

The method may further include the step of: producing further replica microfluidic devices by repeating the isothermally to heating steps with the same mould.

In an further embodiment, the invention provides a method of manufacturing a replica micro-needle for communicating fluids, the method comprising the steps of:

a) casting a mould in a resilient material from a master die of a microneedle, the die having a microneedle body having at a first end a pointed tip to penetrate an epidermal layer, a base at an opposing second end of the body, and an open channel extending along a side of the body from the first end to the second end;

b) moulding a warm thermoplastic into the mould to form the replica microneedle; and c) separating the moulded replica microneedle from the mould.

In another aspect, the invention provides a replicated microfluidic device made according to the method described herein.

In a further aspect, the invention provides a replica microfluidic device including: a plurality of micro-needles across a support member; at least one reservoir in the support member; and a channel providing fluid communication between at least one micro-needle and at least one reservoir; wherein a first aspect ratio to approximately at least 1400:1 of at least one protruding feature of the master die of the micro-fluidic device is also the aspect ratio in the replicated micro-fluidic device.

The first aspect ratio may be to a height of the plurality of micro-needles to a radius of curvature of a tip of the plurality of micro-needles.

The device may further include a second aspect ratio of a replicated reservoir feature of: a depth to a width is approximately at least 5:1.

The device may further include a third aspect ratio of a replicated bore or a replicated lumen of: a depth to a diameter is approximately at least 20:1.

The device may further include at least one fine feature resolution of at less than 500 nanometres of the master die of the microfluidic device is also replicated in the replica micro-fluidic device.

The device wherein a height of the plurality of micro-needles of the replica micro-fluidic device may be in the approximate range of 650 to 1000 micro-metres.

The device wherein a depth of a reservoir of the replica microfluidic device may be at least 100 micrometres.

The device wherein a depth of the open channel may be in the approximate range of 20 to 100 micrometres.

The device wherein each micro-needle of the microfluidic device may have a yield strength of at least approximately one Newton.

The device wherein a surface of the at least one reservoir and the at least one channel may be hydrophilic and the other surfaces of the microfluidic device are hydrophobic.

In another aspect, the invention provides a microneedle for communicating fluids comprising: a body having at a first end a pointed tip to penetrate an epidermal layer; a base at an opposing second end of the body; and an open channel extending along a side of the body from the first end to the second end; wherein the channel is configured to communicate fluids between the tip and the base of the microneedle.

In a further aspect, the invention provides a patch comprising an array of microneedles, as described in any one of the preceding claims, the plurality of microneedles are supported on a support member.

The plurality of open channels may extend into the support member of the patch form a channel network in communication with at least one reservoir.

The channel network in the patch may be pre-treated to react to a presence of a predetermined substance within the bodily fluid.

The pre-treatment may be a gel containing at least one reagent for an analyte detection.

In another aspect, the invention provides: a method of replicating a microfluidic device substantially as described herein; a replica microfluidic device substantially as described herein; a microneedle substantially as described herein; a patch substantially as described herein; a microfluidic device substantially as described herein; and a microblade substantially as described herein.

According to a further embodiment of the invention, there is provided a microneedle for communicating fluids comprising: a body having at a first end a pointed tip to penetrate an epidermal layer; a base at an opposing second end of the body; and an open channel extending along a side of the body from the first end to the second end, wherein the channel is configured to communicate fluids between the tip and the base of the microneedle.

The microneedle of the present invention provides an alternative to a hypodermic needle that minimises the pain experienced by a subject when the epidermis is punctured to access subcutaneous fluids in the body. The microneedle is so small and/or smooth and/or sharp that a single microneedle or a plurality of microneedles can be inserted through the epidermal layer with minimal, if any, sensation of the epidermal layer being pierced.

A further advantage of the invention is directed to reducing the requirement for a skilled operator when accessing subcutaneous fluids, as the microneedle ameliorates the necessity to find and correctly penetrate an individual vein. The microneedle or a plurality of microneedles can be simply located on the epidermal layer or skin of the subject at virtually any accessible location. This makes the fluid collection or introduction of fluids into a subject a simpler procedure and reduces the opportunity for error.

In order to draw blood and interstitial fluid subcutaneously, the microneedle must be sufficiently long to penetrate the subcutaneous capillary plexus. However, it must also remain sufficiently narrow so as to minimise pain when piercing the epidermal layer. When increasing the length to width ratio of the microneedle, the geometry of the microneedle becomes more susceptible to buckling. The microneedle of the present invention is configured and fabricated to provide the above advantages while reducing, if not eliminating buckling.

This microneedle provides an open channel that draws fluid along the microneedle by virtue of capillary action. The configuration of the open channel in the surface of the microneedle removes geometrical design constraints associated with hollow needles and further enables manufacturing techniques that were previously not applicable to hollow needle and hypodermic manufacture.

In one embodiment the base is provided on a support member. The base could be integrally formed with the support member In one embodiment, the base of the microneedle is flared outwardly. Alternatively or additionally, the base of the microneedle includes a peripheral annular skirt at the second end of the body.

The open channel may in one embodiment extend along the pointed tip of the microneedle.

The microneedle may further comprise a reservoir. The reservoir of the microneedle may be disposed within the base of the microneedle and is configured to collect bodily fluids. The reservoir may alternatively be configured to store a fluidic medicament to be delivered subcutaneously.

In one embodiment, the microneedle is solid. The microneedle may be substantially cylindrical. The pointed tip of the microneedle could be conical and/or the pointed tip of the microneedle could be eccentrically disposed relative to a central axis of the microneedle.

The microneedle may comprise a plurality of open channels extending along the body, where the plurality of open channels may be equidistantly spaced around the perimeter of the microneedle.

In one embodiment the open channel may be configured to have a rounded cross-section. The open channel preferably extends linearly along the microneedle. Alternatively, the open channel encircles the microneedle.

The open channel may extend into the base of the microneedle, and can transition into a reservoir of the microneedle, specifically in the base of the microneedle or in the support member. The open channel increases in width as it extends into the base of the microneedle.

In one embodiment, the plurality of open channels within the body of the microneedle may communicate with a single reservoir.

In an embodiment, the depth of the open channel in the body of the microneedle may be about 30 µm. The surface of the microneedle may be hydrophilic or at least partially hydrophilic.

The microneedle may be treated in various ways. For example, a portion of the outer surface of the microneedle may be treated with a surfactant. Alternatively, an outer surface of the microneedle may be treated with a metal coating. Furthermore, an outer surface of the microneedle may be treated with oxygen plasma to electrostatically charge the surface. Further still, an outer surface of the microneedle can be treated with an acid, or a base or an acid based solution.

In another embodiment of the invention there is provided a patch comprising an array of microneedles, the array of microneedles being supported on a support member.

By combining a plurality of microneedles into an array, a greater quantity of subcutaneous fluids can be communicated at any given time. The plurality of microneedles are each configured to have an open side channel that communicates bodily fluid by capillary wicking. These open channels form a network of collection reservoirs along the plurality of microneedles and across the support member.

Each of the microneedle and/or the support member can be provided with a reservoir, configured: to collect fluid from surrounding microneedles; to disperse fluids and medicament subcutaneously; or partially filled with colorimetric or fluorimetric reagents for measuring analyte concentrations in subcutaneous fluids, as drawn.

The ability to treat the surface of the microneedles and/or the reservoirs by placing reactants within the open channel network facilitates point-of-care treatment and diagnostics. There can be a significant time delay between the drawing of fluids and the results of the testing of the fluids. Time delays increase the inefficiencies in the treatment/diagnostic process and as such providing results faster and eliminating the opportunity for samples being mixed-up are all advantages of the microneedle of the present invention.

In one embodiment, an open channel of each of the plurality of microneedles extends from the base of the microneedle into an open channel in the support member. The plurality of microneedles and the open channel extend across a collection face of the patch. The plurality of open channels in the support member may extend across the support member of the patch forming a channel network, where the channel network comprises a plurality of microneedles and reservoirs.

In another embodiment, a single reservoir within the channel network may be in direct fluid communication with at least four microneedles, simultaneously.

The reservoir in one embodiment may be configured to be closed, having a sealed bottom configured to store fluid. The open channels of the support member may transfer fluid across the support member to a region on the collection face of the patch where analysis or assay can be carried out. Alternatively, the support member may comprise through channels to provide at least one passage from the collection face of the patch to a reverse face of the patch, where assay or analysis may be conducted. The reverse face of the patch may be configured to fluidically communicate with a vessel for collecting fluid from multiple reservoirs.

In one embodiment, the reservoir volume may be at least 1 nanolitre.

In a further embodiment each pair of microneedle may be configured to communicate with a single reservoir. A network of channels preferably provides communication to and from a plurality of reservoirs In other embodiments, the open channels may transition into a reservoir such that a meniscus of the fluid within the channel is curved away from the direction of travel of the fluid. The direction of fluid flow in the open channel is towards the gas phase provided the meniscus is concave.

In another embodiment, the reservoir may be pre-treated to react to the presence of a predetermined substance within the bodily fluid. Further, the channel network may be pre-treated to react to the presence of a predetermined substance within the bodily fluid. Further still, the pre-treatment could be a gel containing reagents for analyte detection.

In a further embodiment of the invention there may be provided a method of manufacturing a microneedle for communicating fluids, the method comprising the steps of: (a) casting a mould in a resilient material from a die of a microneedle, the die comprising a microneedle body having at a first end a pointed tip to penetrate an epidermal layer, a base at an opposing second end of the body, and an open channel extending along a side of the body from the first end to the second end; (b) moulding a warm thermoplastic on the mould to form a microneedle; and (c) separating the moulded microneedle from the mould.

This embodiment of the invention may facilitate the manufacture of microneedles and microneedle arrays that are sufficiently long to penetrate the subcutaneous capillary plexus of a subject, by replication from a 3D lithographic die. This embodiment of the invention may facilitate the implementation of geometric designs directly without the manufacturing constraints imposed by conventional machining or etching processes.

Typically submicron structures are formed by deep reactive ion etching or laser milling. However laser milling is expensive and ill-suited to high volume production. Further, deep reactive ion etching is hard to control and does not provide geometric accuracy or control over the geometry and dimensions of a final product. By producing the 3D die using stereo lithography, a submicron resolution can be achieved in the finished microneedle or microneedle array that is not commercially achievable through hollow needle manufacturing processes. The array of microneedles is integrally formed with the support member, having a plurality of reservoirs therein and a network of open channels communicating across the entire support member between the individual microneedles.

The microneedle or patch is formed in a thermoplastic material and can be commercially replicated by a process of soft embossing. The 3D die or Master is replicated in a resilient material e.g. a silicone elastomer which is then used as a mould for the thermoplastic embossing (or soft embossing technique). The process of soft embossing is particularly beneficial for the moulding of delicate, fragile microstructures because the resilient mould is elastomeric. This reduces the opportunity for damage to the fragile microstructure when de-moulding the formed microneedles. The open channel design of the microneedle is well suited for soft-embossing to manufacturing a high precision, high quality, high volume microneedle.

One embodiment of the method may include forming the die using stereo lithography or 3D printing. The resilient material of the mould could be a silicone rubber and the thermoplastic of the microneedle would be of a medical grade.

The method may further includes hot embossing the thermoplastic with the mould to form the microneedle.

The method may further comprises the step of cooling the thermoplastic microneedle prior to separation from the mould.

The method may include forming a master die from the mould in a hard material (polymer casting or electroplating).

Further forms of the invention are as set out in the appended claims and as apparent from the description.

BRIEF DESCRIPTION OF THE DRAWINGS

The description is made with reference to the accompanying drawings, of which.

DETAILED DESCRIPTION OF EMBODIMENTS

The present invention will now be described more fully hereinafter with reference to the accompanying drawings, in which various embodiments of the invention are shown. The Summary of the Invention description is to be included in this Detailed Description. The invention may be embodied in many different forms and should not be construed as limited to the embodiments set forth herein.

It is intended that all references in this specification to "bodily fluids" are intended to encompass blood, interstitial fluids and other liquids to be drawn from the body for medical testing and diagnostic procedures. It is further intended that references to "bodily fluids" and "an epidermal layer" are intended to encompass human bodies, animals and other living organisms.

The epidermal layer is intended to reference the 'tough' outer part of the skin that will pose the most resistance to microneedle penetration into the dermis, wherein the dermis contains capillaries. The epidermal layer is sometimes referred to as the 'skin epithelium' and the layer below the epidermis (which contains the blood vessels) is referred to as the 'dermis'.

Figure 1:
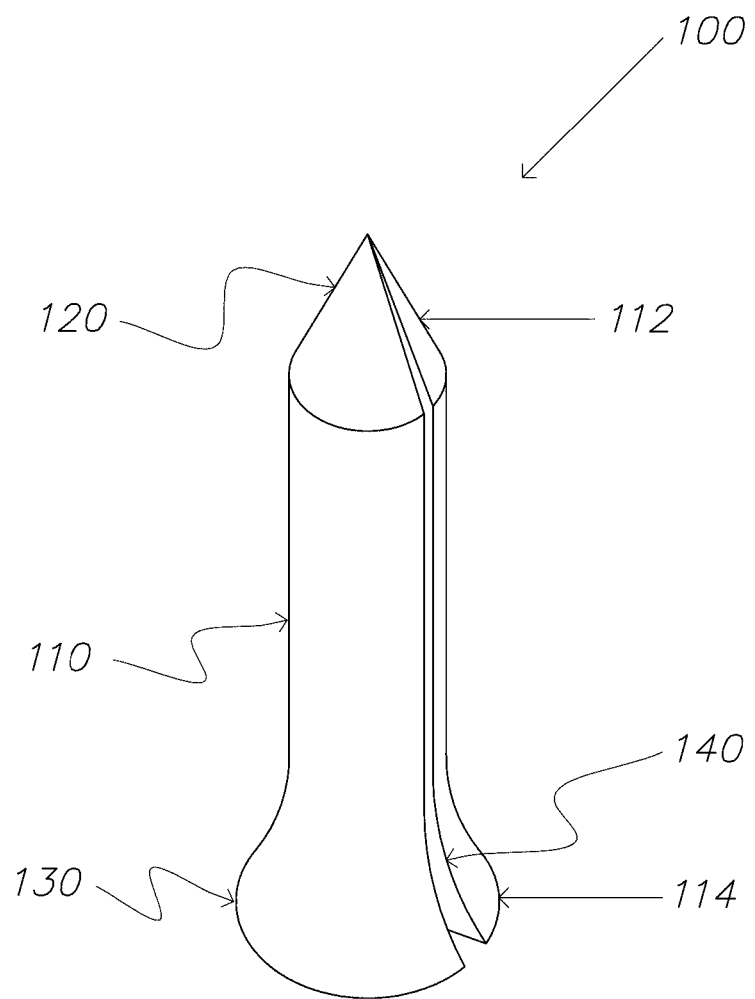
FIG. 1 is a perspective view of a microneedle, according to a first embodiment of the invention.
Figure 2A:
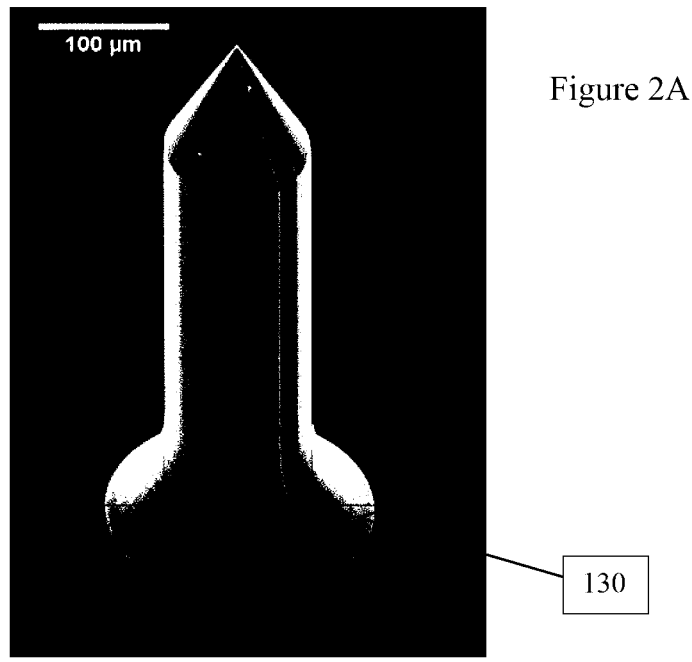
FIG. 2A-2E are perspective views taken with a scanning electron microscope (SEM) of actual microneedles from FIG. 1, illustrating variations in the ratio between a tip and a body of the microneedle.
Figure 2B:
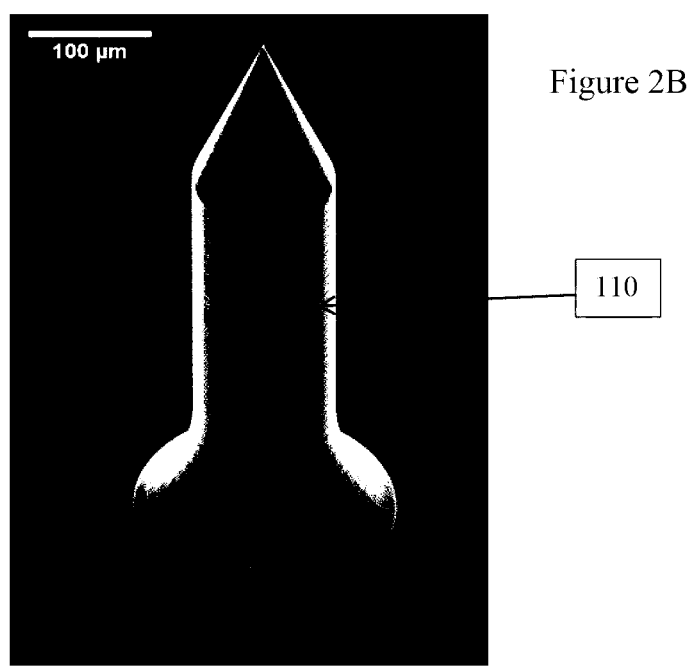
Figure 2C:
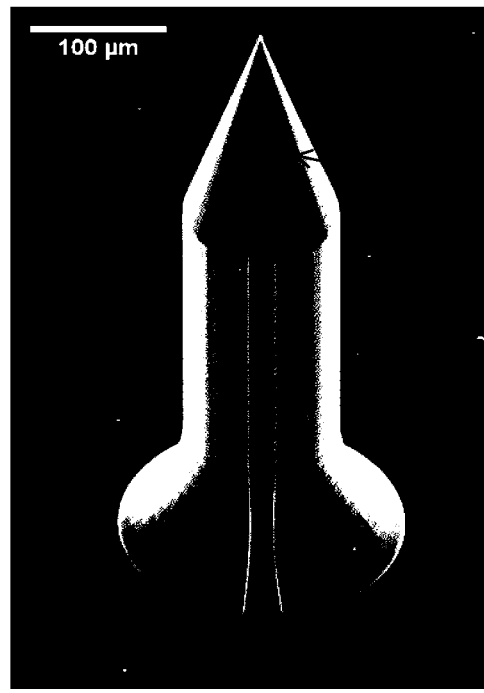
Figure 2D:
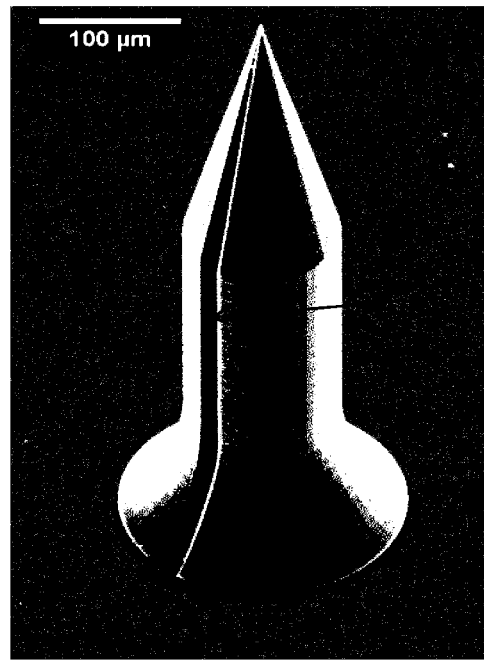
Figure 2E:
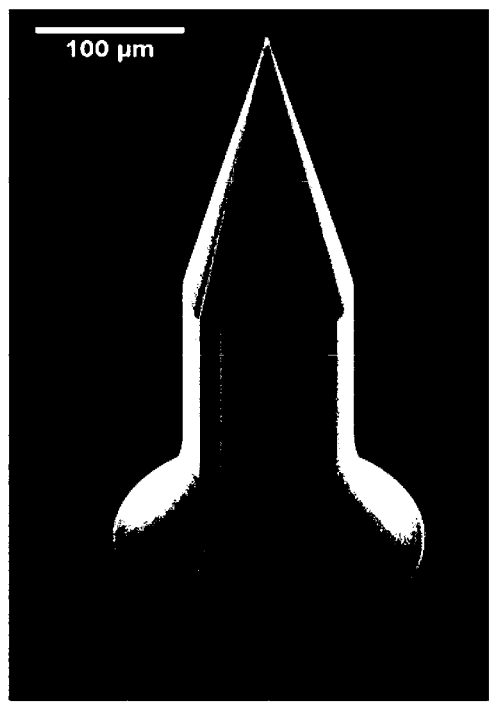

Referring now to FIG. 1 a schematic diagram of a microneedle 100 for communicating bodily fluids comprising: a body 110 having at a first end 112 a pointed tip 120 to penetrate an epidermal layer; a base 130 at an opposing second end 114 or base of the body 110; and an open channel 140 extending along a side of the body 110 from the first end 112 to the second end 114, wherein the channel 140 is configured to communicate bodily fluid, collected subcutaneously, from the tip 120 to the base 130 of the microneedle 100. That is bodily fluids may be sampled by the microneedle sufficiently penetrating the skin.

FIG. 1 shows the cylindrical tip 120 having a point centred at the first end 112 of the body 110. It is also contemplated (although not illustrated) that the pointed tip 120 can be eccentrically disposed relative to the body 110 without departing from the invention.

In this embodiment, the body 110 of the microneedle 100, illustrated in FIG. 1, is cylindrical. However an ovoid or quadrilateral section to the body 110 can be utilised to communicate subcutaneous fluids. In contrast to a hypodermic needle and in light of the dimensions of the microneedle 100, subcutaneous penetration can still be achieved where the body 110 of the microneedle 100 does not have a constant transverse cross-section 115 i.e. is not cylindrical, for example a microblade as described below with respect to FIGS. 32 to 35.

The base 130 of the microneedle 100 extends outwardly from the second end 114 of the body 110, providing an annular skirt to the microneedle 100. A smooth transition between the body 110 and the flared base 130 minimises stress concentration within the body 110 when the microneedle 100 is loaded. The microneedle 100 is primarily exposed to two main load conditions: the first is experienced when the microneedle 100 is manufactured; and the second is experienced when the microneedle 100 is puncturing the epidermal layer of a subject. The load conditions on the microneedle 100 are shown in further details in FIGS. 3 and 4.

Fluid to be communicated via the microneedle 100 can be applied to or recovered from the base 130 of the microneedle 100. Although not shown in FIG. 1, a reservoir 150 can be incorporated into the base 130 of the microneedle 100 specifically for the accumulation of fluids. Various forms of reservoirs for fluid sampling and drug delivery are described with respect to FIGS. 9 to 12 and further herein.

The microneedle 100 is contemplated to be manufactured to provide a variety of embodiments in which the ratio between the length of the body 110 and the length of the tip 120 is varied. FIGS. 2A to 2E are scanning electron microscope photographs of a number of actual embodiments of the microneedle 100, corresponding to the dimensions in Table 1.

TABLE 1

| FIG. | Total height | Tip height | Body height | Base height | Body diameter | Base diameter | Groove diameter |
|---|---|---|---|---|---|---|---|
| 2A | 700 μm | 150 μm | 400 μm | 150 μm | 150 μm | 280 μm | 30 μm |
| 2B | 700 μm | 200 μm | 350 μm | 150 μm | 150 μm | 280 μm | 30 μm |
| 2C | 700 μm | 250 μm | 300 μm | 150 μm | 150 μm | 280 μm | 30 μm |
| 2D | 700 μm | 300 μm | 250 μm | 150 μm | 150 μm | 280 μm | 30 μm |
| 2E | 700 μm | 350 μm | 200 μm | 150 μm | 150 μm | 280 μm | 30 μm |

The groove diameter (Table 1) or open channel 140 depth may vary from approximately 20 to 100 micrometres in the examples provided herein for the microneedles.

From Table 1 a ratio between a thickness of the body of the microneedle and a height of the pointed tip of the microneedle would preferably fall within the ranges from 1:1 to 1:5, while a ratio of a height of the head of the microneedle and a length of the body, could be between 5:1 and 2:1. The ratio of a length of the microneedle and a width of the microneedle may be about 5:1.

In terms of the finest feature resolution for the master die, as described elsewhere herein, the sharpness of the tip may be to a radius of curvature of 500 nm. An ultra-sharp, replicated micro-needle tip is described below with respect to FIG. 25. Accordingly an aspect ratio between the largest feature of the total height of 700 micrometres for a micro-needle from Table 1 and the smallest feature of the tip point of a micro-needle may be approximately 1400:1. This provides an example of the dynamic range of the new and improved embossing technique's reproduction range for producing replica micro-needles as described further below. The micro-needle aspect ratio example is to a protruding feature for replication. Further examples to aspect ratios for the dynamic replication range for cavities or recesses of the new embossing technique are provided below with respect to: FIGS. 9 to 12 for the reservoirs, for cavities, bores and recesses, and further to more micro-fluidic devices for FIGS. 25 to 27.

As the length of the tip 120 increase the diameter of the body 110 remains constant. This varies the gradient of the conical tip 120 providing a stubby tip 120 to the microneedle 100 in FIG. 2A, where the slope of the tip 120 is approximately 1:1. In contrast, the microneedle 100 illustrated in FIG. 2E has a tip 120 that slopes with a gradient of approximately 7:3.

By varying the ratio of the tip 120 to the body 110, different characteristics can be achieved in relation to the ease of introduction of the microneedle 100 into the epidermal layer and the flow rate at which fluids can be communicated. Examples of such characteristics are dimensions, shape and surface finish of the microneedle. Accordingly, the characteristics of the microneedle 100 can be designed to the procedures to be carried out and the nature of the fluids to be communicated for sampling or drug/delivery agent.

The geometric details of the microneedle 100 embodiments illustrated in FIG. 2 are based upon an understanding of the material properties of the thermoplastic material of the microneedle 100 and the fluid dynamic properties of open channel 140 flow.

There are a number of material considerations that will determine the geometrical features of the microneedle 100. Specifically, these are length, tip sharpness and hardness, shaft radius, flared base, open channel configuration and channel flow. These features will now be described in more detail.

Fluid collection or sampling of blood requires penetration of the skin to a depth of typically at least 650 microns so that the subcutaneous capillary plexus is penetrated by the microneedle tip 120. Thus the length of the microneedle 100 for blood collection may be at least 650 microns. In contrast, collection of interstitial fluid without blood contamination may require penetration of skin to a depth less than 650 microns. Thus the length of the microneedle 100 for interstitial fluid collection may be between 200 and 600 microns.

The needle tip 120 will penetrate the epidermal layer if it exerts tensile stress at the point of contact which is beyond the ultimate strength of skin. This is approximately 30 MPa for an average human subject. Of course, the ultimate strength of skin depends on age and body location. However, the sharper the needle tip 120, the more concentrated the tensile force at the point of contact.

The tip 120 must be harder than the skin for penetrate to occur. The modulus of elasticity for skin, for an average human subject, is between 25-100 kPa. When the microneedle 100 is manufactured from cyclic olefin polymer Zeonor® the recorded tensile modulus of the microneedle 100 is 2200 MPa. Thus, the tensile modulus of the plastic microneedle 100 is four orders of magnitude higher than skin, and sufficiently capable of penetration.

It is undesirable to increase the thickness or radius of the body 110 of the microneedle 100, as this will increase the sensation of penetration for the subject when the microneedle 100 punctures the epidermal layer. However, as the length of the microneedle 100 is increased to penetrate the necessary subcutaneous depth of 650 microns, the microneedle 100, specifically the microneedle body 110 may become increasingly more susceptible to buckling. The effects of buckling on the microneedle 100 can lead to difficulties during use of the microneedle 100 and can also cause problems for the manufacture of the microneedle 100; specifically, de-moulding of the finished microneedle 100. These problems with the prior art have been overcome with the invention.

In one embodiment the microneedle 100 is made from a thermoplastic material such as Zeonor®. Zeonor® has a tensile strength of 54 MPa; therefore, the microneedle 100 when loaded should avoid stress concentrations that exceed this value.

The microneedle 100 is more likely to fail at locations where stress is concentrated, namely at sharp corners or geometrical transitions such as the point where the microneedle body 110 flares outwardly to form the base 130. Further stress concentration areas can be formed where the micro-needle 100 is connected to a support member 160 (as described in further embodiments in relation to a patch 105 or micro-fluidic devices described herein. Cracks that will initiate microneedle 100 failure will also propagate from regions of maximum tensile stress.

Figure 3:
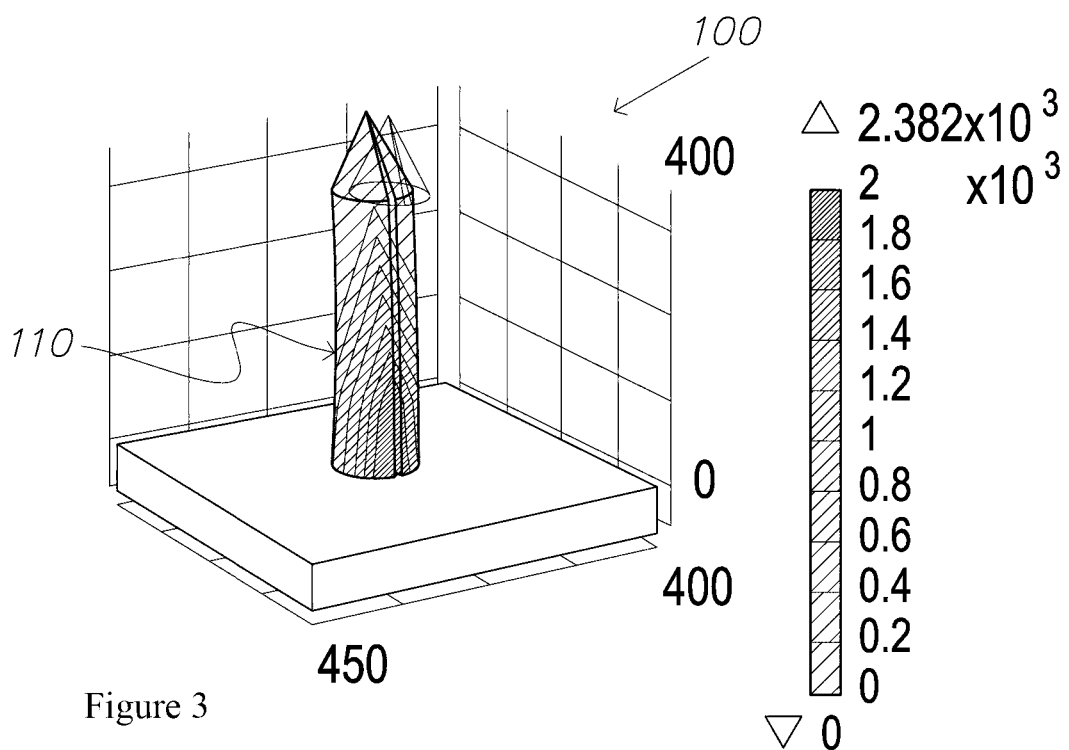
FIG. 3 is a 3D finite element model (FEM) of a microneedle according to an embodiment of the invention, illustrating bending and surface stress concentration under lateral-tip load conditions.

A Finite Element Analysis (FEA) was performed on a model of the microneedle 100 when manufactured from Zeonor® 1060. As illustrated in FIG. 3, the highest surface stress (von Mises) were found to occur at the transition between the body 110 of the microneedle 100 and support member 160 when a lateral load of $7.5 \times 10^{-4}$ N was applied to the tip 120 of the microneedle 100. It is concluded that, the microneedle 100 is most likely to fail at the point of highest stress when laterally loaded at its tip 120. This load case simulates the forces that may be experienced during the de-moulding process for manufacturing the microneedle 100 and the puncturing of skin.

Figure 4:
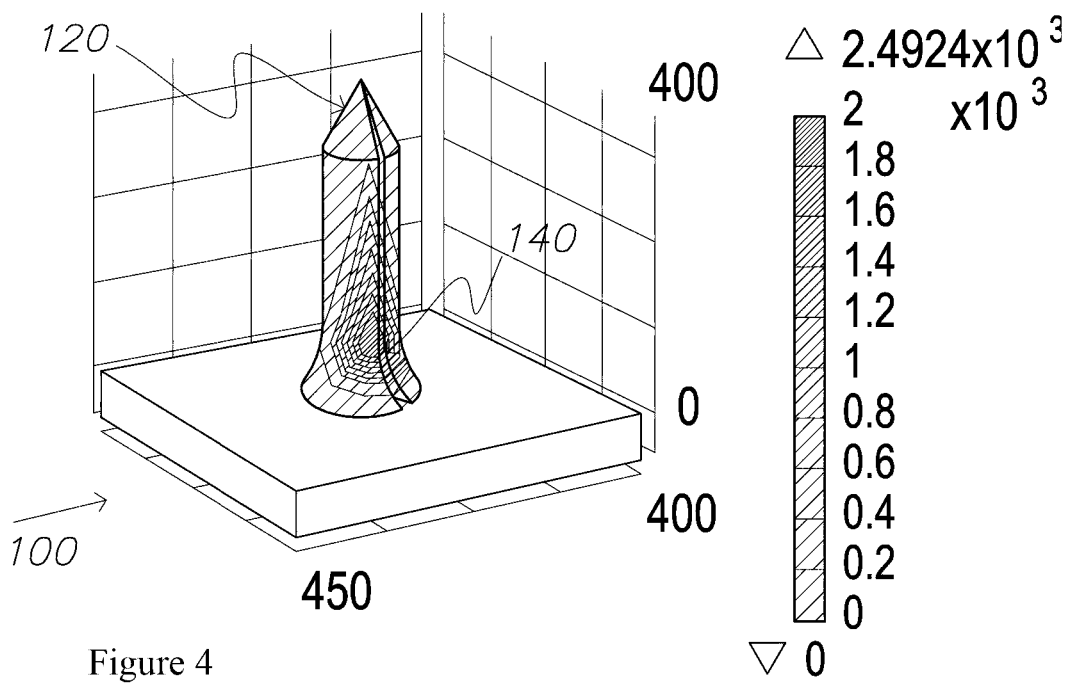
FIG. 4 is a 3D FEM of the microneedle of FIG. 1, illustrating bending and surface stress concentration under lateral-tip load conditions about the flared base of the microneedle.

The contoured regions of the microneedle 100 in FIG. 4 represent regions of von Mises stress along the microneedle 100 when laterally loaded at the tip 120. Comparing the contours around the base 130 in FIG. 3 and FIG. 4, the stress contours can be seen to diffuse across the base 130 and are generally less in magnitude due to the flared base 130 gradually transitioning the microneedle 100 into the support member 160 or substrate.

Accordingly, FIG. 3 strongly suggests that without the flared base 130, the microneedle 100 may be susceptible to breaking at its base 130 because the surface stress is at least 20 mPa. For the flared base 130, the maximum stress achieved is 10 mPa and occurs just above the transitions between the base 130 and the body 110. Thus flaring the base 130 of the microneedle 100 to provide a curved flange to transition into the support member 160 will strengthen (avoid stress concentration) at the connection of the microneedle 100 to the support member 160 as illustrated in FIGS. 3 and 4.

Aside from potential failure from point loading and stress, the microneedle 100 may fail due to buckling if the shaft radius of the body 110 is too small for the applied force. The critical load force F for bucking is calculated by Euler's formula:

$$F = \frac{\pi^2 EI}{(KL)^2}$$

Here E is the modulus of elasticity of the plastic, I is the area moment of inertia, L is the shaft length, and K as constant called the effective length factor which depends on the mode of column support. This scenario occurs where the base 130 of the microneedle 100 is fixed in all directions, whilst the tip 120 is free to move laterally (K=2). Sample values for a microneedle 100 in accordance with some embodiments of invention are shown in Table 2, below.

TABLE 2

| Property | Symbol | Value |
|---|---|---|
| Shaft radius | R | 75 m$^{-6}$ |
| Length | L | 650 m$^{-6}$ |
| Area moment of inertia for a circle | I | $\frac{\pi}{2}R^4$ |
| Effective length factor | K | 2 |
| Modulus of elasticity (cyclic olefin polymer Zeonor ®) | E | 2100 MPa |
| Critical load force for needle buckling | F | 0.61 N |

Assuming that the needle tip 120 contact area is 1 μm$^2$, then the skin pressure at the critical buckling load will be 10$^6$ MPa, which is at least four orders of magnitude higher than the ultimate strength of skin (30 MPa).

Although hollow microneedles 100 can be formed using a 3D stereo lithographic process the internal lumens can be difficult to accurately replicate when using high volume production techniques.

For example: a 3D master die was created of a hollow microneedle and the mould was then filled with a PDMS material to form a negative mould. Although the external form of the microneedle was closely replicated, the flow of material through the central core, or lumen of the microneedle, became lodged within the lumen and made the PDMS material difficult to remove for some of the hollow microneedles.

Soft-embossing is a technique for transferring form to a material. It can be conducted on hot or cold material and conveys the shape of a mould to the material to be moulded via pressure. However, replicating hollow microneedles 100 by soft-embossing is problematic due to the fragility and scale of a microneedle lumen for the negative mould of PDMS.

Accordingly, the microneedle 100 is configured to provide an open channel 140 to communicate fluids along the microneedle 100 and into a reservoir 150 using capillary pressure. An example of such a micro-fluidic device is shown in FIGS. 9 to 12. There is no central lumen, thereby effectively making the microneedle 100 solid and adapted for manufacture via soft-embossing and mass production.

Open channels 140 direct flow from the microneedle body 110 to reservoirs 150 in the base 130 of the microneedle 100. The open channels 140 of the microneedle 100 communicate subcutaneous fluids via capillary action or the "wicking effect". The capillary driving force that drives passive filling of the open channel 140 is generated by the contact angle θ between the fluid and the outer surface 115 of the microneedle 100. The contact angle θ should be less than 90° to generate capillary force for passive filling of the needle. This then defines a hydrophilic surface.

Furthermore the curvature vector of the fluid/air interface (meniscus) should be directed away from the fluid side of the interface for capillary filling as defined by the Young-Laplace equation.

$$\Delta P = -\gamma \nabla \cdot n = -\gamma \left( \frac{1}{R_1} + \frac{1}{R_2} \right) \qquad \text{Eq. 1}$$

Where n is a unit vector normal to the surface (directed away from fluid into the gas phase), ∇ is the divergence operator, γ is the surface tension (72×10$^{-3}$ N/m) for water/air, 56×10$^{-3}$ N/m for fluid/air), and $R_1$ and $R_2$ are the principle radii of the surface. If $R_1$ and $R_2$ are negative they are convex up with respect to the fluid surface, and so the pressure inside the fluid is less than in the gas phase (ΔP>0).

For a hydrophilic surface, fluid does not leak from open channels provided the pressure inside the fluid is below a critical leakage pressure $P_{leak}$ which depends on the width w of the open part of the channel, the surface tension of the fluid γ and the contact angle. Accordingly for $P_{leak}$ $$P_{leak} = \frac{2\gamma \sin(\theta)}{w} \qquad \text{Eq. 2}$$

Figure 5:
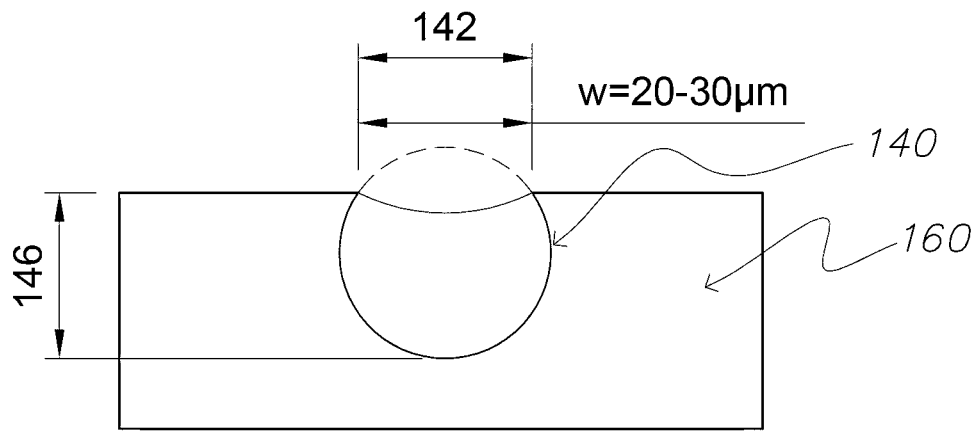
FIG. 5 is a sectional view of an open channel of the microneedle, illustrating fluid in the channel exhibiting a concave meniscus.

An example of a width for an open channel 140 draining of microneedles is around 20 μm. FIG. 5 shows a cross-section through an open channel 140 which may have circular or a square profile. The bold peripheral line around the channel 140 indicated the wetted wall of the channel 140.

The leakage pressure if the contact angle is 67.5° and the surface tension is 56×10$^{-3}$ N/m is around 5 kPa. Capillary pressure is around 30 mm Hg (4 kPa) so it is likely that the open channel 140 will not leak provided the surface tension is not too low, and the channel width 142 is in the range of 10-20 μm.

Figure 5A:
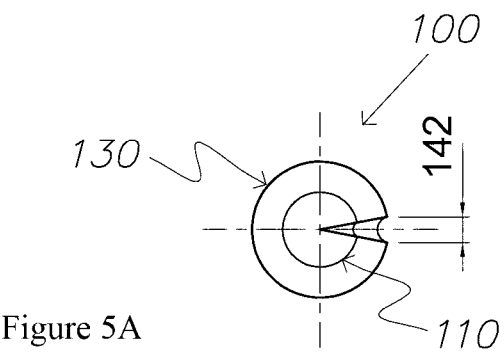
FIG. 5A is a plan view of the microneedle of FIG. 1, illustrating the configuration of an open channel extending along the body of the microneedle.

FIG. 5A illustrated a cross-sectional view of an open channel 140 extending along a body 110 of the microneedle 100. The width 142 of the channel 140 is 24 μm.

The rate of capillary driven filling of microneedle 100 with fluid is dependent on a number of factors: the contact angle)(<90°, the viscosity of the fluid, and the capillary radius. It will take about 18 milliseconds for a 650 μm long channel 140, having a width 142 of 30 μm, and a contact angle 67.5° to fill.

In later embodiments an array of microneedles 100 are, preferably integrally, formed on a support member 160 to produce a patch 105. For such embodiments, the reservoir 150 can be formed in the support member 160, in the plane of the support member 160 (see FIG. 9). Where an array of microneedles 100 are provided on a support member 160 the open channel 140 of each microneedle 100 extends from the body 110 and the base 130 into the support member 160 to communicate/transfer fluid to and from the reservoir 150. The microneedles 100, open channels 140 and the reservoir 150 are disposed on a collection face of the patch 105. In this patch 105, the channel 130 changes direction by 90° as it transitions from the body 110 of the microneedle 100 to the support member 160. A width 142 and a depth 146 of the channel 140 will then increase as the channel 140 goes through a transition 148 and leads to the reservoir 150 to maximise the volume of fluid that can be collected.

At points along the open channel 140 where cross-section increases, the curvature of the meniscus will decrease, and therefore, the capillary pressure will also be reduced. Maintaining a concave meniscus will allow fluid flow to continue within the open channels 140. Accordingly, the direction of fluid flow is towards the gas phase provided the average curvature of the fluid meniscus is concave (Eq. 1).

Figure 6:
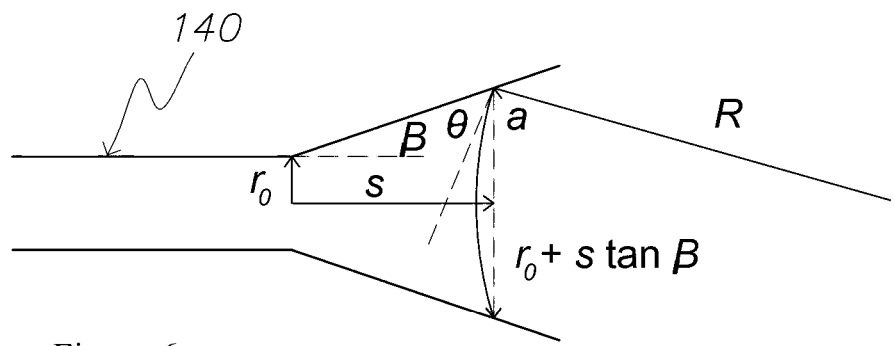
FIG. 6 is a schematic representation of a fluid meniscus in an open divergent channel.

A radius of a circular cross-section of channel 140 should not increase at a greater rate than a critical value determined by the contact angle θ of the fluid and the channel wall 144. The rate of channel divergence is defined by the angle it subtends with the centreline. If the sum of the contact angle θ between the fluid meniscus and channel wall 144 and the channel divergence angle β as shown in FIG. 6 is less than 90°, then the meniscus will continue to be concave, and will draw fluid along the diverging channel 140.

$$\theta + \beta < 90° \qquad \text{Eq. 3}$$

The capillary pressure $P_c$ drawing fluid for an axisymmetric diverging channel is:

$$P_c = \gamma \times \frac{1}{R} = \gamma \times \frac{\cos(\theta + B)}{r_0 + s\tan\beta} \qquad \text{Eq. 4}$$

Where γ is surface tension, $$\frac{1}{R}$$

is the curvature of the meniscus, $r_0$ is the inlet radius of the diverging channel, and s is the distance along the diverging channel.

The same formula can be applied to diverging parallel plates where $a_0$ is half the plate separation at the entry to the diverging plates:

$$P_c = \gamma \times \frac{1}{R} = \gamma \times \frac{\cos(\theta + B)}{a_0 + s\tan\beta} \qquad \text{Eq. 5}$$

Figure 7:
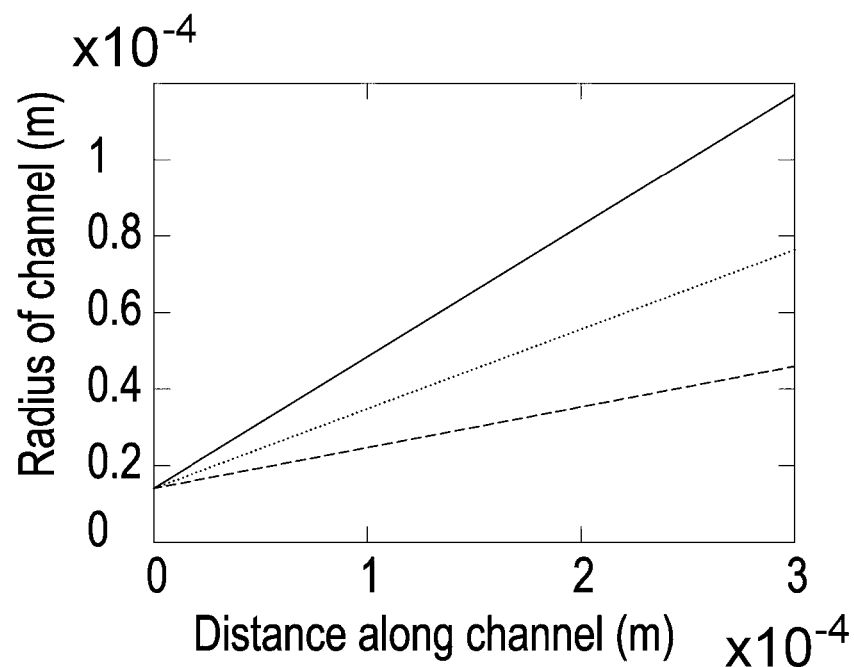
FIG. 7 is a graph illustrating how a divergence angle of an open channel varies in relation to a radius and a distance along the channel.
Figure 8:
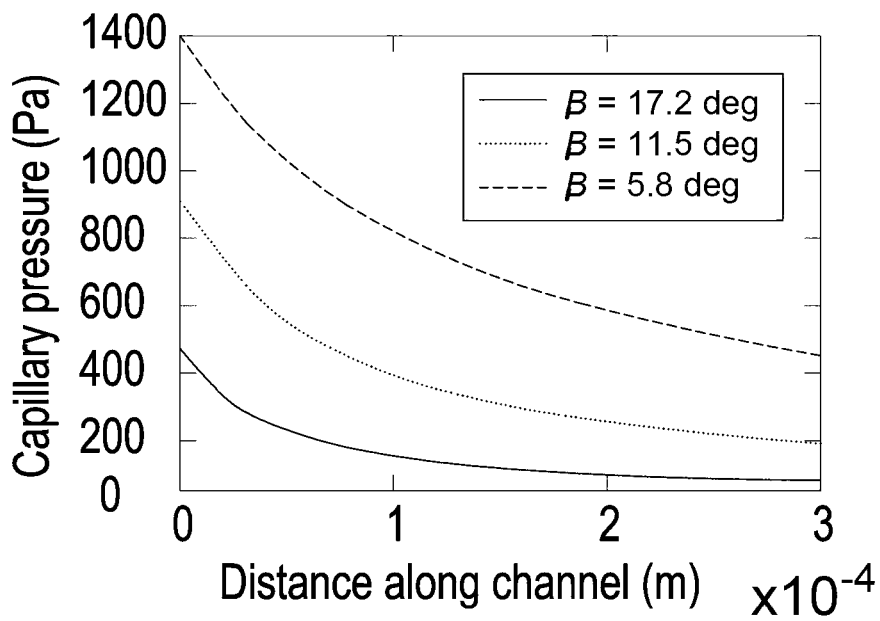
FIG. 8 is a graph illustrating how the divergence angle varies in relation to capillary pressure and a distance along the open channel.

Capillary pressure decreases as the angle of divergence increases. Also the capillary pressure will decrease along the channel as illustrated graphically in FIGS. 7 and 8.

The Capillary pressure can be approximated for a rectangular cross-section with high aspect ratio using the above Eq. 5. Where $\alpha_0$ is half the plate separation (shorter side of the rectangular cross-section). For open channel flow the capillary pressure will be less than the value for closed channel flow and is approximated by the wetted perimeter ratio (see FIG. 5).

$$P_c[\text{open channel}] \cong \frac{\text{wetted perimeter}}{\text{total perimeter}} P_c[\text{closed channel}] \qquad \text{Eq. 6}$$

Blood or interstitial fluid accumulates in the reservoirs 150 from a subcutaneous space of the body. It is important that the reservoir 150 can accumulate a sufficient volume of fluid to facilitate meaningful analysis.

In one embodiment, the reservoir 150 has a depth 152 of 100 µm, a width 154 of 100 µm and a length 156 of 100 µm, thus providing a nanolitre volume. As described above, the width 154 of the reservoir 150 is restricted by the divergence angle of the channel 140 leading into the well.

In one embodiment, the open channel network 149 of the support member 160 can be initially filled with a gel or surface treated with reagents for analyte detection. The analytes are then transported to the reservoirs 150 by diffusion. Accordingly, this embodiment provides a method for continuous monitoring of small molecules such as glucose, electrolytes or other metabolites in the drawn subcutaneous fluid.

In another embodiment, the individual reservoirs 150 can be configured to provide an inlet and an outlet (open or closed) thereby providing a passage through the substrate of the microneedle 100 or the support member 160 such that subcutaneous fluid can be drawn into a vessel on the back-side (or reverse face) of the microneedle 100. The reverse face of the patch 105 opposes the collection face of the patch 105 from which the microneedles 100 extend. This vessel can be used to collect fluid for transportation or can contain an analyte sensor for point-of-care testing.

Capillary pressure is the driving force that generates flow of blood or interstitial fluid into open channel fluid collection network 149 (see Eq. 7). The Hagen-Poiseuille equation is the physical law that give the pressure drop ΔP for fully established laminar flow along a cylindrical pipe. It is applied here to estimate the rate of filling of the open channel fluid collection network 149.

$$\Delta P = \frac{8\mu L Q}{\pi r^4} \qquad \text{Eq. 7}$$

Where L is the length of the fluid column inside the tube, µ is fluid viscosity, Q is flow rate and r is the radius of the channel.

Assuming that capillary pressure is equal to the pressure drop along the pipe (i.e. Eq. is equal to Eq. 7) then:

$$v(L) = \frac{r\gamma\cos\theta}{8\mu L} \qquad \text{Eq. 8}$$

Where v(L) is the average velocity of the gas fluid interface.

Thus the air/blood interface velocity is approximately inversely proportional to length of the fluid column and viscosity, and directly proportional to the radius of the channel and capillary pressure. The filling time is found by integrating with respect to channel length:

$$T_{fill} = \int_0^L \frac{dx}{v(x)} = \frac{4\mu L^2}{r\gamma\cos\theta} \qquad \text{Eq. 9}$$

The Reynolds number for channel flow is then:

$$Re = \frac{2v(L)r\rho}{\mu} = \frac{r^2 \rho \gamma \cos\theta}{4\mu^2 L} \qquad \text{Eq. 10}$$

Table 3 below provides typical values for channel flow driven by capillary pressure.

TABLE 3

| Parameter | Value |
| --- | --- |
| Viscosity of blood ($\mu$) | $4 \times 10^{-3}$ Pa·s |
| Density of blood ($\rho$) | 1060 kg/m$^2$ |
| Length of liquid column in channel (L) | $0$-$10^{-3}$ |
| Blood surface tension ($\gamma$) | $55 \times 10^{-3}$ N/m |
| Contact angle ($\theta$) | $45°$-$89°$ |
| Channel radius (r) | $15$-$50 \times 10^{-6}$ |
| Blood/air interface velocity (L = 600 μm) | $16 \times 10^{-3}$ m/s |
| Filling time (L = 600 μm) | $18 \times 10^{-3}$ s |
| Reynolds number | 0.13 |

As shown above, the expected filling time for the open channel 140 of the microneedle 100 is 18 milliseconds.

Microneedles 100 manufactured from thermoplastic polymers such as cyclic olefin polymer Zeonor® are hydrophobic. To provide all of the advantages as described above, surface modification is required to decrease the contact angle θ to less than 90° for capillary filling of the microneedle 100.

The advantage of a very hydrophilic surface (wetting angle around 30°) is a higher capillary pressure drawing fluid into the microneedle 100. Furthermore, the channel network 149 can have a greater divergence angle (Eq. 4) and thereby provide faster filling. However a low wetting angle will lead to a reduction in the leakage pressure (Eq. 2). Thus selection of an optimal contact angle is always a compromise between leakage and filling.

There are a number of chemical and physical methods for converting hydrophobic to hydrophilic surfaces. These include:
 a) deposition of a metal layer such as gold or silver;
 b) oxygen plasma treatment of the surface to introduce positive and negative charge to the surface;
 c) an ion implantation by focused plasma;
 d) treatment of the surface with a surfactant (amphiphilic molecule such as Pluronics); and
 e) chemical modification of the surface with strong bases or acids.

In the later examples to the performance of the microfluidic device option b) was done to convert the surfaces of the replica micro-fluidic device made of the thermoplastic cyclic olefin polymer Zeonor from hydrophobic to hydrophilic as follows. Surface modification to decrease the contact angle below 70° for capillary filling of the device was done with oxygen plasma treatment. Oxygen plasma treatment was performed on the Zeonor micro-fluidic devices for 20 minutes using an oxygen plasma etcher/asher (PE-250 Plasma etcher, Denton vacuum, USA) with 50 W RF power and 340 mTorr pressure. The oxygen ashing treatment resulted in a drop in contact angle below 70° for at least 2 weeks.

Alternatively only the inner surfaces of the reservoirs and the open channels may be treated to render them hydrophilic. The inner surfaces of the reservoirs and open channels being used to communicate or transfer bodily fluids or medicaments/drugs. Furthermore the other surfaces of the microfluidic device may be left comparatively hydrophobic in order improve the leakage pressure for the channels and reservoirs. The difference in hydrophobicity between the inner surfaces and the outer surfaces of the microfluidic device may contribute substantially to the efficiency of fluid transfer and capacity, particularly with the increase in the respective leakage pressures for the channels and the reservoirs.

Some bodily fluids e.g. blood, can wet hydrophobic surfaces because it contains proteins that act as surfactants. In these cases where blood is to be communicated, it is not necessary to modify the surface 115 of the microneedle 100.

Surface chemistry can also be used to introduce non-fouling layers, such as polyethylene glycol and selective ligands such as antibodies, recombinant fusion proteins with analyte binding domains (e.g., single change Fv antibodies). The reservoir 150 can also be modified with gold nano-patterning that dramatically amplifies adsorbed or fluorescent signals by the induced surface plasmon.

The microneedle 100 can be configured in an array comprising a plurality of microneedles, as previously described coupled to the support member 160. An embodiment of the microneedle 100 array is illustrated as a patch 150 in FIG. 9.

The microneedle patch 105 is an array of microneedles 100 connected to a plurality of reservoirs 160 using an open channel network 149. The microneedle patch 150 consists of the following elements:
 a) An array of microneedles 100 each microneedle having at least one open side channel 140 for drawing blood or interstitial fluid.
 b) At least one closed reservoir 150 for collecting/measuring blood analyte in situ (point-of-care diagnostics) or at least one open reservoir 150 for connecting the reservoir 150 to the backplane of the patch 105 where fluid and cells can be collected for analysis.
 c) Support member 160 connecting the array of microneedles 100 to the at least one reservoir 150.

Referring to FIGS. 9 to 17, various embodiments of the microneedle patch 105 are illustrated. To increase blood collection volume, more than two microneedles may be used. To increase blood collection time, more than one microneedle 100 is connected to each reservoir 150. In one embodiment two microneedles 100 are connected to each reservoir 150 (see FIG. 12). The dimensions of the reservoir 150 are typically 100×100×100 μm to provide a volume of 1 nanolitre. Alternatively a microblade design with more than one microchannel may be used to increase blood volume as described with respect to FIGS. 32 to 35.

Figure 10:
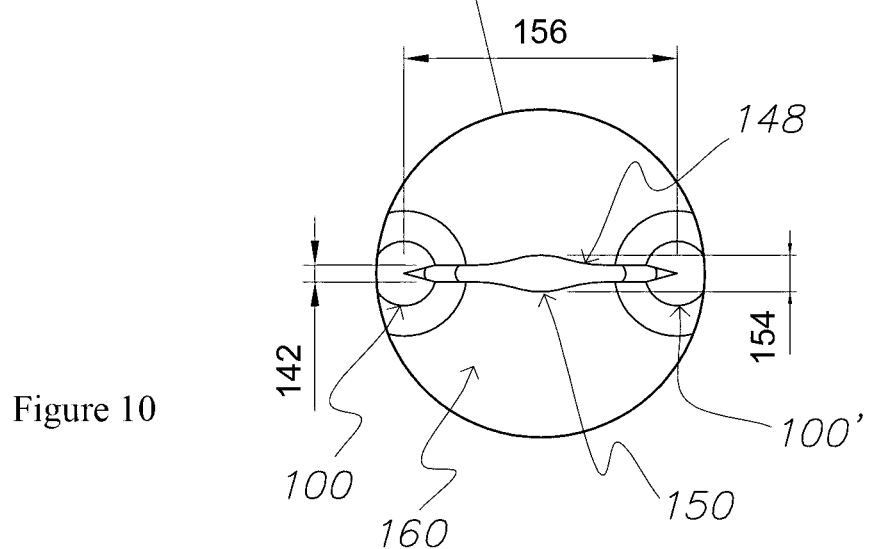
FIG. 10 is a magnified plan view from within the circle of FIG. 9, illustrating two microneedles communicating with a single reservoir via open channels of the patch.
Figure 12:
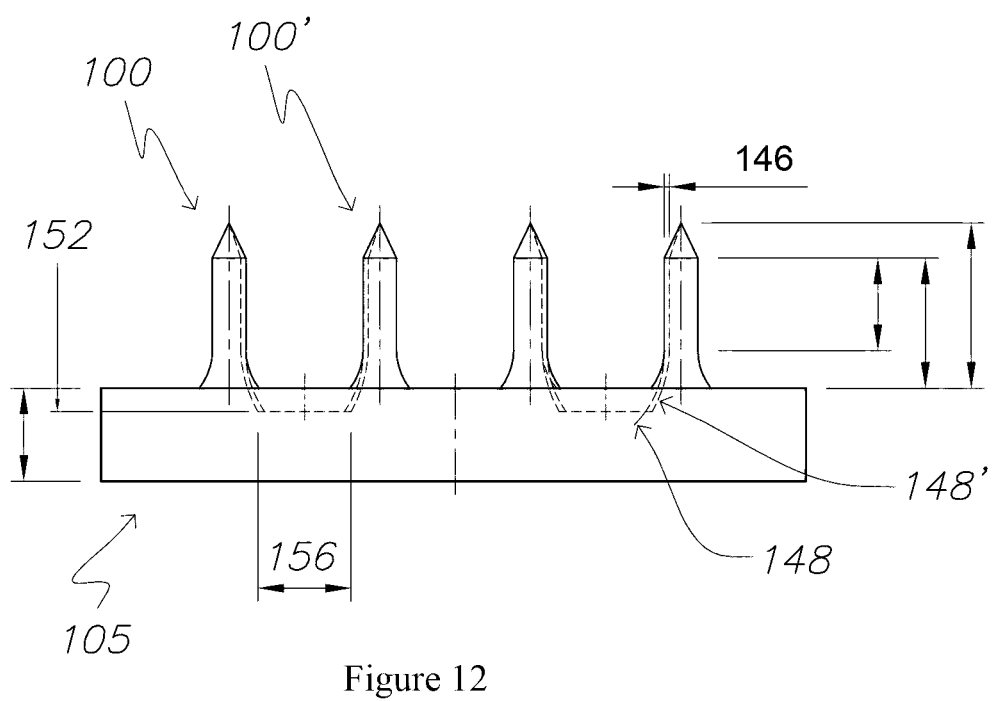
FIG. 12 is a side view of the patch of FIG. 9, illustrating the spatial relationship between the microneedles which are paired to each reservoir.

FIG. 10 illustrates a plan view of a reservoir 150 extending between two microneedles 100. The open channel 140 remains at a constant width 142 as the channel 140 extends along the microneedle 100. The channel 140 smoothly transitions from the microneedle 100 into the support member 160 of the patch 105 and begins to diverge as it traverses the support member 160. The channel 140 finally transitions into the reservoir 150, which is disposed approximately half way between the two microneedles 100. The width 142 of the channel 140 is about 20 micrometres. The depth of the channel or reservoir 140 is shown in FIG. 12 and is approximately 100 micrometres. Accordingly the aspect ratio for the reservoir depth to width is 5:1, that may be accurately replicated by the new embossing technique described herein. The radius of the reservoir 150 is approximately 130 microns.

Figure 11:
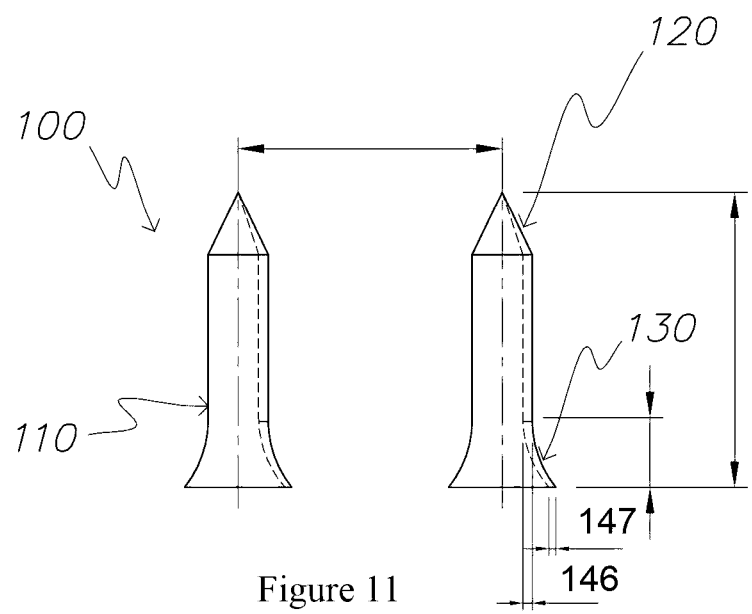
FIG. 11 is a side view of a pair of microneedles according to FIG. 1.

FIG. 11 illustrates a pair of microneedles 100 the centre lines of the two microneedles 100 being disposed 630 microns apart. The depth 146 of the channel 140 as it extends along the body 110 is approximately 30 microns. The depth 147 of the channel 140 through the base 130 reduces to 24 microns. The overall length of the body 110 is 700 microns. The length of the tip 120 is 150 microns. The length of the base 130 of the microneedle 100 is about 150 microns.

FIG. 12 illustrates a pair of reservoirs 150, shown in dotted line, each penetrating the support member 160 to a depth 152 of about 100 microns. FIG. 12 also illustrates a transition radius at the point where the open channel 140 diverges into a reservoir 150. The inner radius of this transition 148 is about 404 microns and the outer radius of the transition 148' (measured from the base of the open channel) is about 430 microns. The transitional radius is shown in the front view of FIG. 12, as the curve that connects the bottom of the channel 140 to the bottom of the reservoir 150.

Figure 9:
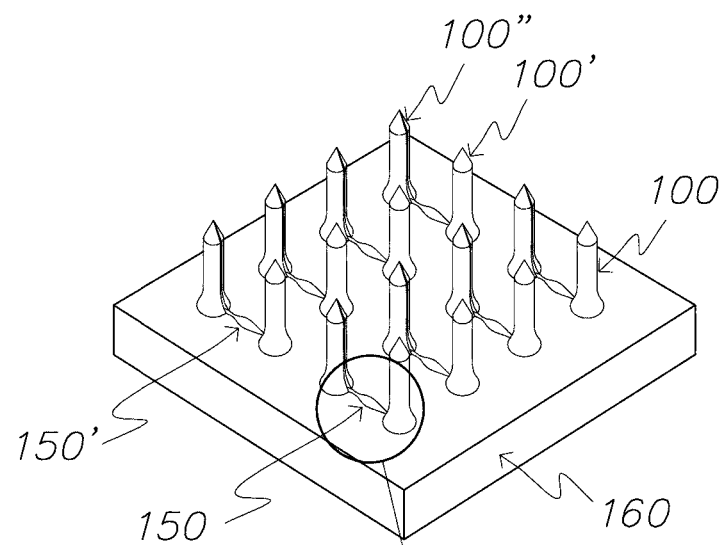
FIG. 9 is a perspective view of a patch according to a second embodiment of the invention, comprising an array of microneedles coupled to a support member.
Figure 13:
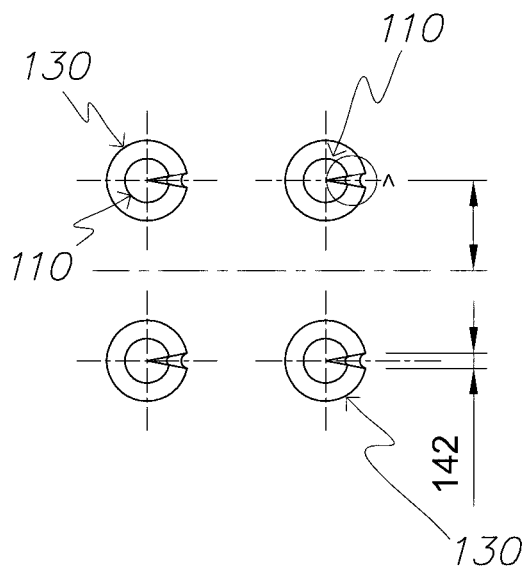
FIG. 13 is a top view of a patch comprising an array of four microneedles.

FIG. 13 illustrates a top view of the patch 105 of FIG. 9. From this perspective it can be seen that the flared base 130 of the microneedle 100 is almost twice the width of the body 110. The base 130 of the microneedle 100 flares from a radius of 75 microns to a radius of 140 microns at the connection plane between the base 130 and the support member 160.

The channel 140 has a width 142 of 40 microns when measured at the connection between the base 130 and the support member 160.

Figure 14:
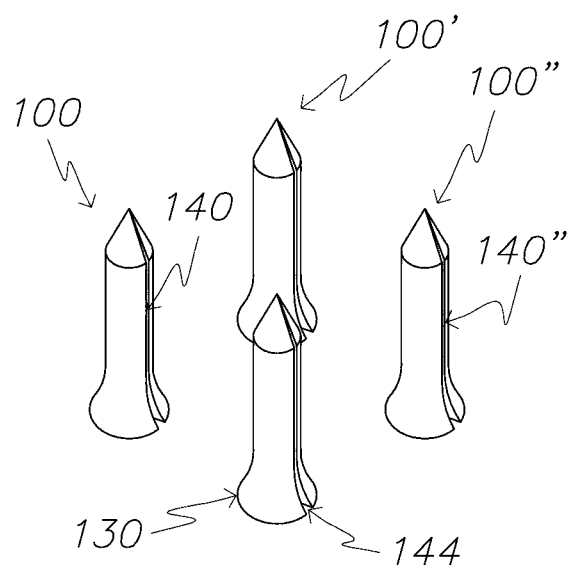
FIG. 14 is a perspective view of the patch of FIG. 13.
Figure 15:
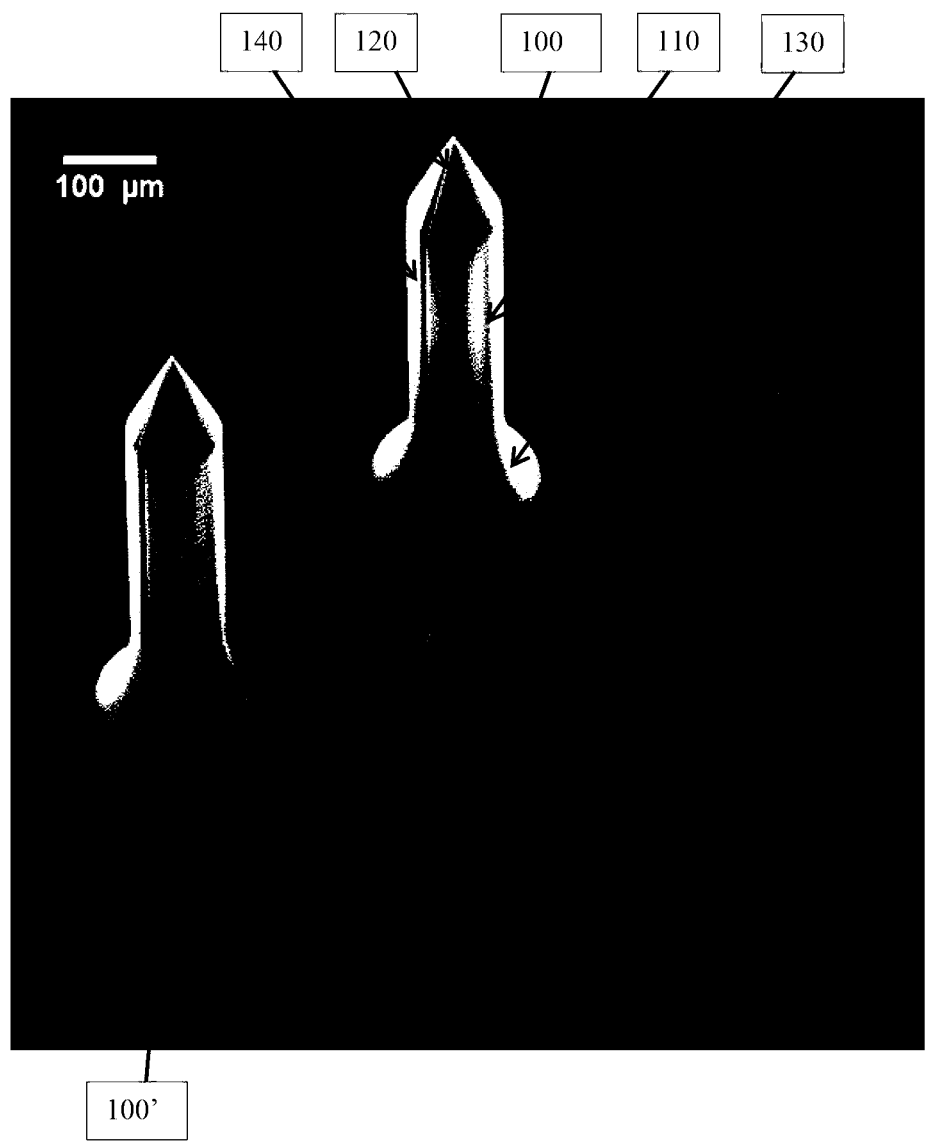
FIG. 15 is an SEM photo of the patch of FIG. 13.

FIGS. 14 and 15 illustrate a perspective view of a four microneedle array. In contrast, FIG. 16 illustrates a patch 105 having a 32 microneedle array and an open channel network 149 connecting three or four microneedles 100 to each reservoir 150.

Figure 16:
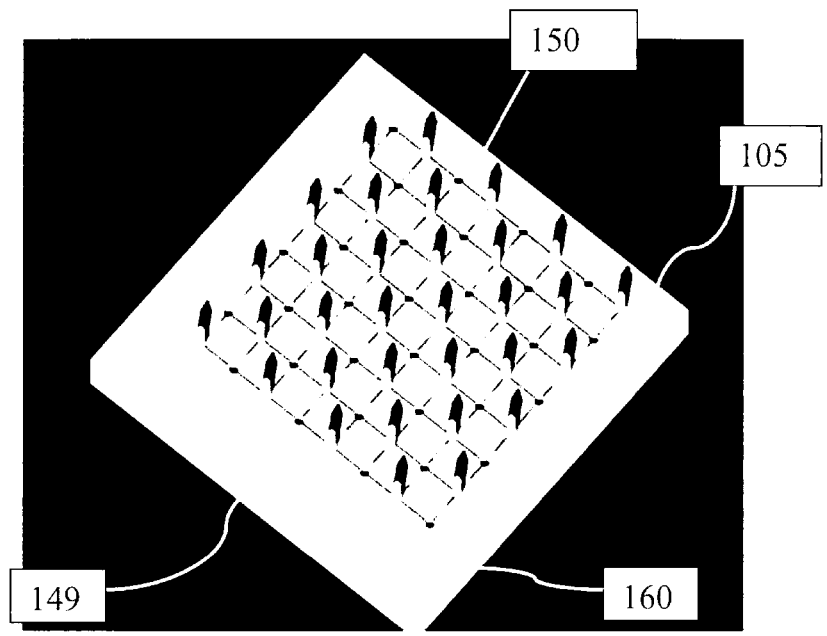
FIG. 16 is a perspective view of a patch comprising a multi-microneedle array coupled to a support member, illustrating the spatial relationship between the plurality of microneedles and reservoirs and the open channel network therebetween.

FIG. 16 is a perspective view of a multi-microneedle array coupled to a support member, illustrating the spatial relationship between the plurality of microneedles and reservoirs. The open channel network 149 is distributed across the support member 160 in a regular grid-like pattern wherein microneedles and reservoirs 150 are alternated at each adjacent cross-section along the grid. In this manner the reservoirs 150 around the periphery of the patch 105 will each communicate with three microneedles 100 and the reservoirs in the centre of the patch 105 will each communicate with four microneedles 100. This reduces the time required to take a subcutaneous fluid sample.

Figure 17:
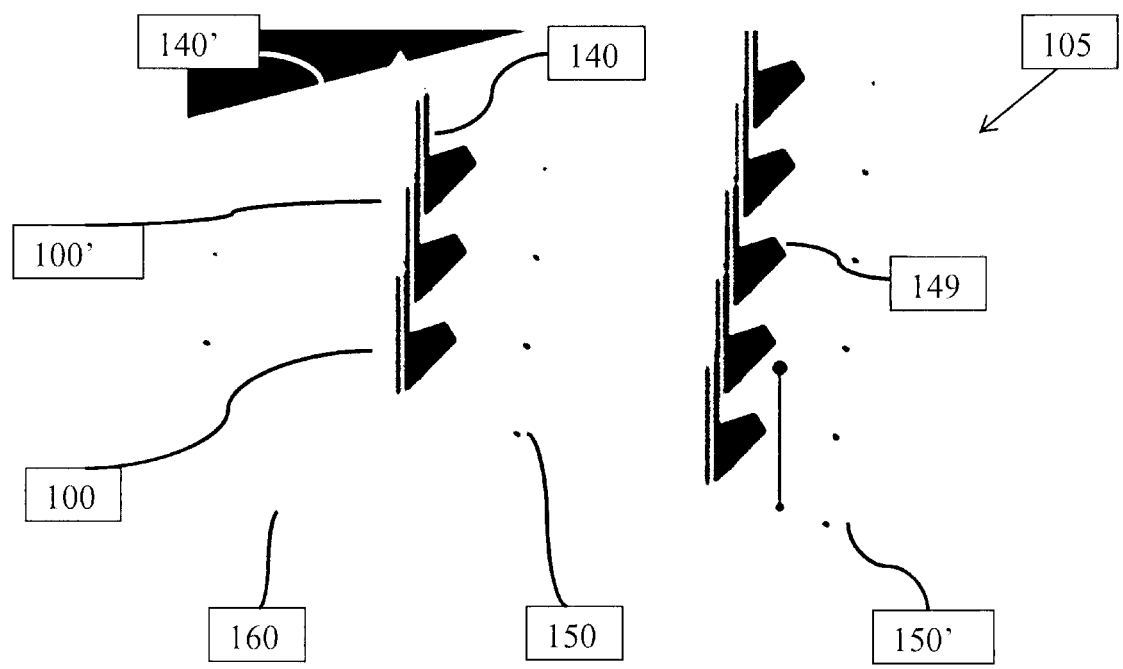
FIG. 17 is a magnified perspective view of the patch of FIG. 16, illustrating a plurality of open channels extending along each microneedle of the patch.

FIG. 17 is a magnified perspective view of the patch 105 of FIG. 16. In this embodiment each microneedle 100 has at least three open channels 140 extending along the length thereof. The microneedle 100 positioned in the centre of the patch 105 having four open channels 140 extending thereon. The microneedle 100 positioned on the periphery of the patch 105 having three open channels 140 extending thereon. By combining a plurality of microneedles 100 with a plurality of reservoirs 150 more efficient collection times can be achieved, thus making the procedure more efficient and less traumatic for the subject.

The collection reservoirs 150 in FIG. 17 may be to be open, partially open or closed depending on whether subcutaneous fluids are to be tested in situ or collected into a vessel for off-site testing. To transport off-site the evaporation from the reservoirs may have to be reduced for designs with open reservoirs. In one alternative the reservoir may be partially closed by forming a master die reservoir with a re-entrant shape. That is the uppermost opening of the reservoir is narrower than the widest breadth of the rest of the reservoir, or a partially closing lip is formed about the upper opening of the reservoir. In another alternative a water impermeable membrane may be bonded onto the top of the channels and/or reservoirs. In yet another alternative the whole microfluidic device after use may be immersed in an oily solution to prevent evaporation during transport.

Figure 18:
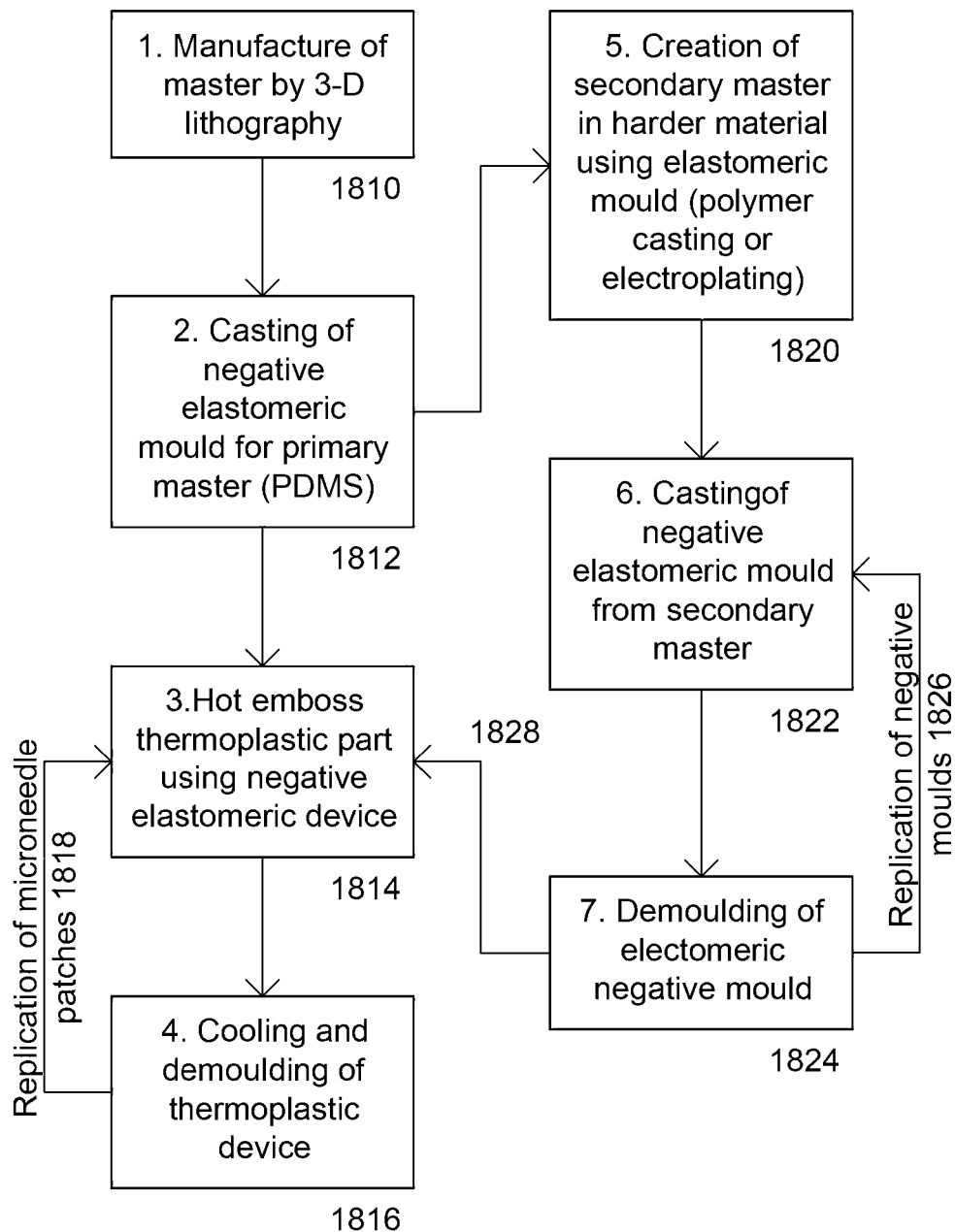
FIG. 18 is a flowchart illustrating process steps in the manufacture of a microneedle or microneedle array, according to an embodiment of the invention.

Also described herein with respect to FIG. 18 and further is a method of manufacturing a microneedle 100 for communicating bodily fluids. The method broadly comprises the steps of:
(a) casting a mould in a resilient material from a master die or original of a microneedle 100, the microneedle 100 having a body 110 having at a first end 112 a pointed tip 120 to penetrate an epidermal layer, a base 130 at an opposing second end 114 of the body 110, and an open channel 140 extending along a side of the body 110 from the first end 112 to the second end 114;
(b) applying a warm thermoplastic into the negative mould to form a replicated microneedle 100; and
(c) separating the moulded microneedle 100 from the negative mould.

A microneedle 100 having a length of at least 650 microns will penetrate the subcutaneous capillary bed. Previously attempted methods for manufacturing microneedles 100 at the lengths sufficient to penetrate the subcutaneous capillary bed, including Deep Reactive Ion Etching (DRIE) or conventional 3D printing, were not capable of providing sufficient geometrical precision or dimensional accuracy to produce the desirable characteristics for microfluidic devices mentioned earlier here. That is the flexibility and precision to formed shapes and recesses. In addition, the sharpness of penetrating microneedles and the smooth surface finish of the microneedle shaft.

Deep reactive ion etching (DRIE) is a popular method used to fabricate microneedles 100 in the prior art. Using DRIE Microneedle 100 geometry is dictated by the physics of isotropic and anisotropic etching which are generally poorly understood. Anisotropic etching is used to generate the microneedle body 110, generating the vertical side-walls. In contrast, the microneedle tip 120 is defined by the isotropic etching process and microneedles 100 longer that 500 microns may not be achieved with geometric stability or precise reproduction capability.

3D lithography is capable of providing submicron resolution but has a slow printing rate that renders it unsuitable for economic mass production. For example a single microneedle 100 may take between 10 and 40 minutes to fabricate. Whilst a micro fluidic device with an array of many microneedles and reservoirs may take many hours. However, the presently disclosed method uses 3D lithography to manufacture a precise master die of a photoresist, which incorporates optimal geometric designs for skin penetration and collection of subcutaneous fluids. The photoresist master die may then be used to produce a replica micro-fluidic device using an improved process to "soft embossing". The improved process of soft embossing may allow for economic mass production of micro-fluidic devices.

3D lithography takes computational data and applies the dimensions and details directly to form a 3D model. This affords geometrically accuracy of submicron resolution that can provide microneedles 100 that are sharp enough to penetrate the skin with low force. The application of 3D lithography to microneedle manufacture has the following advantages:
a. Computer aided design (CAD) of optimal needle geometries using structural analysis of needle strength and skin penetration force. These designs can be accurately manufactured off the electronic drawings.
b. Design of open channels 140 for wicking fluid flow by capillary action down the side of the microneedle 100 into reservoirs 150 for analyte analysis.
c. CAD of complex micro-fluidic devices.

A disadvantage of 3D lithography is that the master die formed of photoresist may be brittle and unsuitable for biomedical applications. Also for 3D lithography there is a trade-off between resolution and rate of manufacture rate. To this end using an improved 'soft embossing' to manufacture microneedles 100 and micro fluidic devices from medically approved thermoplastic polymers provides the manufacturing precision of 3D lithography of the master die with the volume production of the improved soft embossing replication process. The thermoplastic material chosen for the replica micro fluidic devices further provides superior mechanical properties to the 3D lithographic UV curable resin/photoresist used to produce the master die form of the micro fluidic device.

The soft embossing process shown in FIG. 18 includes the following steps:

a. Casting 1812 a silicone rubber negative mould from the 3D lithographic master die 1810, 1910;

b. Hot embossing 1814 a medical grade thermoplastic polymer (e.g. cyclo-olefin polymer) into the silicone rubber negative;

c. Allowing the thermoplastic polymer to cool to room temperature 1816; and d. Gently de-moulding 1816 the set thermoplastic microneedle 100 without fracturing the microneedles.

Alternatively to step b. above an ultra-violet light (UV) curing or catalyst curing may be used with the appropriate resin or plastic, instead of heating a thermoplastic above its glass transition temperature. At step c. then the curing agent may then be applied as appropriate, for example a UV light or a pre-mixed catalyst would be timed to gel and harden the resin at step c.

Advantageously the mould may be re-used (item 1818, FIG. 18) multiple times to emboss and further replicate further micro-fluidic devices. To date the inventors have found that a mould may be re-used over 18 times without noticeable deterioration in the fine or larger features of a micro-fluidic device.

To further scale the manufacturing process of FIG. 18, multiple secondary master dies may be produced 1820 by the new embossing process. The secondary master dies or templates 1820 may be used for manufacture of multiple elastomeric moulds for replicating micro-fluidic devices, via an iterative process as shown in FIG. 18. The secondary master dies may be arranged on a single composite mould as an array so that multiple micro-fluidic devices are manufacture with each embossing cycle. For example, a single master die 1810 may be used to generate 100 secondary masters which may be arranged in an array to form a composite mould. The composite mould may have a 100 by 100 multi-fluidic devices corresponding moulds 1822, 1824, 1826. Accordingly 10,000 replica microfluidic devices may then be generated 1828, 1816 with each embossing cycle using the higher density devices in the alternate composite mould 1822, 1824, 1826.

The silicone rubber of the negative mould can deform with low force. The silicone rubber is pliable to the extent that microneedles 100 and patches 105 can be moulded and de-moulded without damaging the microneedles 100, even when the surface of a patch 105 is not entirely convex. That is, if some re-entrant cavities or recesses are present in the microfluidic device the elastomeric mould material may deform sufficiently to enable its entire removal from a reduced aperture to a reservoir or partially open channel, for example the partially open channel of FIG. 5. This is because the negative mould may deform without applying any significant stress to the microneedles 100.

In a manufacturing process using a silicone negative mould, once cast, may be used to mould numerous microneedle patches. However, the mould has a limited life span and can be damaged or lose dimensional accuracy on de-moulding of the microneedles such that a new silicone negative mould needs to be cast. Accordingly, while a single silicon negative will manufacture a plurality of patches, multiple silicone negatives can be cast to meet the desired production volumes. As described above with respect to FIG. 18.

FIG. 18 provides a flowchart illustrating the process steps in the manufacture of a microneedle 100 or patch 105, according to some embodiments of the invention. The steps of the manufacturing process will now be described in more detail.

Manufacture of a Precision Die by 3-D Lithography

A 3D Laser Lithography system was used to create the microneedles 100 precision die illustrated in FIGS. 2 and 15. The process control parameters are as follow:

63× microscope objective immersed in photoresist

Photoresist: IP-Dip

Laser Power: 80 mW

Scan Speed: 50 mm/s

Slicing Distance: Min=0.5 µm Max=0.7 µm

The 3D Laser was precisely focused to heat and cure the form of a microneedle 100 layer-by-layer (hence, slicing distance) and in this manner a cured 3D microneedle precision die was generated.

Casting of Negative Elastomeric Mould

A soft negative impression of the precision, master die was cast using a silicone elastomer. The preferred material for the master die was a polydimethylsiloxane, (PDMS) supplied as SYLGARD 184 Silicone Elastomer Kit, Dow Corning, Midland, Mich. USA, www.dowcorning.com. The preferred PDMS was used with a base:curing agent ratio of 10:1. The PDMS mould was then degassed in a vacuum chamber at room temperature for approximately one to two hours and subsequently cured at 60° to 65° C. overnight at atmospheric pressure. The mould was then peeled away from the master die. Alternative resilient elastomeric materials for the mould may also include: polyurethane elastomeric alloys, rubber and latex.

Hot Emboss Thermoplastic Part Using Negative Elastomeric Mould.

Initial trials to producing the replicating thermoplastic microneedles by 'soft embossing' was by use of a primitive "Carver" heated press and the cured PDMS negative mould.

Thermoplastic pellets (Zeonor® 1060R) are loaded into the PDMS mould, which is then placed between two stainless steel plates during the soft embossing process. The preferred thermoplastic was a cyclic olefin polymer (COP), branded Zeonor®, by the Zeon Corporation, www.zeon-.co.jp. Alternative materials for forming the microneedle include other medically approved thermoplastics, such as polytetrafluoroethylene (PTFE), polyetheretherketone (PEEK), polystyrene, and polycarbonate.

In order to provide a good (accurate) replica, the embossing force must be high enough to overcome the viscous force of the Zeonor® (or alternate thermoplastic to be hot embossed), such as in the case of a more primitive "Carver" press. The PDMS mould is itself elastomeric with a lower modulus compared to the cooled thermoplastic replica microfluidic device. The modulus of PDMS is in the range 360 to 870 Pa. Care must be taken with the PDMS mould not to exert excessive force when soft embossing with more primitive presses such as the "Carver" press, compared with another re-configured press described further below. Excessive force will result in geometrical deformation of the PDMS mould, and therefore geometrical imperfections in the finished microneedle 100 or patch 105.

In manufacturing prototype microneedles 100, it was found that an embossing force of 150N with an embossing temperature of 100° C. for 30 minutes will produce a consistently good replication. Using the above embossing parameters, no bubbles formed inside the embossed thermoplastic microneedles 100.

Cooling and De-Moulding of Thermoplastic Device.

Following cooling to ambient temperature, thermoplastic needles were peeled off the PDMS elastomeric mould. The elastomeric mould may deform without fracture or defect provided the de-moulding forces are below the tensile strength of the mould. The tensile strength of PDMS is 2.24 MPa.

Further Methods and Apparatus:

In a further embodiment the original micro-needle or micro-fluidic master die was fabricated by two-photon polymerisation using the Photonic Professional GT system (by Nanoscribe GmbH, Germany). Master microneedles were made from a UV-curable photoresist called "IP-DIP" or "IP-S" as developed by Nanoscribe GmbH.

As noted above, this photoresist is may be brittle and not sufficiently robust for producing numerous moulds. As per the description with respect to FIG. 18 a secondary master die may be made from the first master die to form a secondary master die of a stronger, harder, more durable material. This secondary master die may then be used to create multiple silicone moulds in single, double, quadruple form etc. This then may be used to further speed up the manufacturing process as a single silicone mould can be formed to manufacture a plurality of microneedles 100 in a single soft-embossing step.

A micro-needle as part of a micro-fluidic device has been developed for painless skin penetration for transdermal drug delivery or body fluid sampling. The clinical application of micro-needles and/or micro-fluidic devices requires specific geometric features for skin penetration and transport of fluids and molecules between the dermis and the diagnostic or drug delivery parts of a micro-fluidic device. Prior art fabrication methods lacked the precision and speed required for cost-effective and large scale micro-needle array production and micro-fluidic device production. The improved and new embossing described here allows for rapid replication of long (>600 micrometres long or high), slender, mechanically stable and robust micro-needles that can penetrate into the dermis. In addition the replicated micro-needles may also be replicated with microfluidic channels and reservoirs/wells for fluid transport, storage and analysis to form a microfluidic device or patch.

A master die of a micro-fluidic device with micro-needles may be readily produced by an additive fabrication processes such as lithography electroforming fabrication as for example described in: Han, M., D.-H. Hyun, H.-H. Park, S. S. Lee, C.-H. Kim, and C. Kim, "A novel fabrication process for out-of-plane microneedle sheets of biocompatible polymer" Journal of Micromechanics and Microengineering, 2007. 17(6): p. 1184. Alternatively and preferably a two photon polymerisation process may be used, for example: Gittard, S. D., A. Ovsianikov, B. N. Chichkov, A. Doraiswamy, and R. J. Narayan, "Two photon polymerization of microneedles for transdermal drug delivery" Expert Opin Drug Deliv, 2010. 7(4): p. 513-33; Doraiswamy, A., C. Jin, R. J. Narayan, P. Mageswaran, P. Mente, R. Modi, R. Auyeung, D. B. Chrisey, A. Ovsianikov and B. Chichkov, "Two photon induced polymerization of organic—inorganic hybrid biomaterials for microstructured medical devices" Acta Biomaterialia, 2006. 2(3): p. 267-275; and Ovsianikov, A., B. Chichkov, P. Mente, N. A. Monteiro-Riviere, A. Doraiswamy, and R. J. Narayan, "Two Photon Polymerization of Polymer-Ceramic Hybrid Materials for Transdermal Drug Delivery" International Journal of Applied Ceramic Technology, 2007. 4(1): p. 22-29). The preferred master die fabricating technique may accurately and precisely produce specific and novel microneedle and micro-fluidic device features from CAD. However the submicron resolution to 500 nm required for micro-needle and micro-fluidic device manufacture entails printing times that may be many hours for a single device. However such 3D printing technologies may produce a sufficiently robust master die of the micro-needles and micro-fluidic device that may be replicated in mass production. For example a master die micro-needle patch/micro-fluidic device as shown in FIG. 19 was manufactured by the inventors in 22 hours by the Photonic Professional GT system, (Nanoscribe GmbH, Germany, www.nanoscribe.de).

Figure 19:
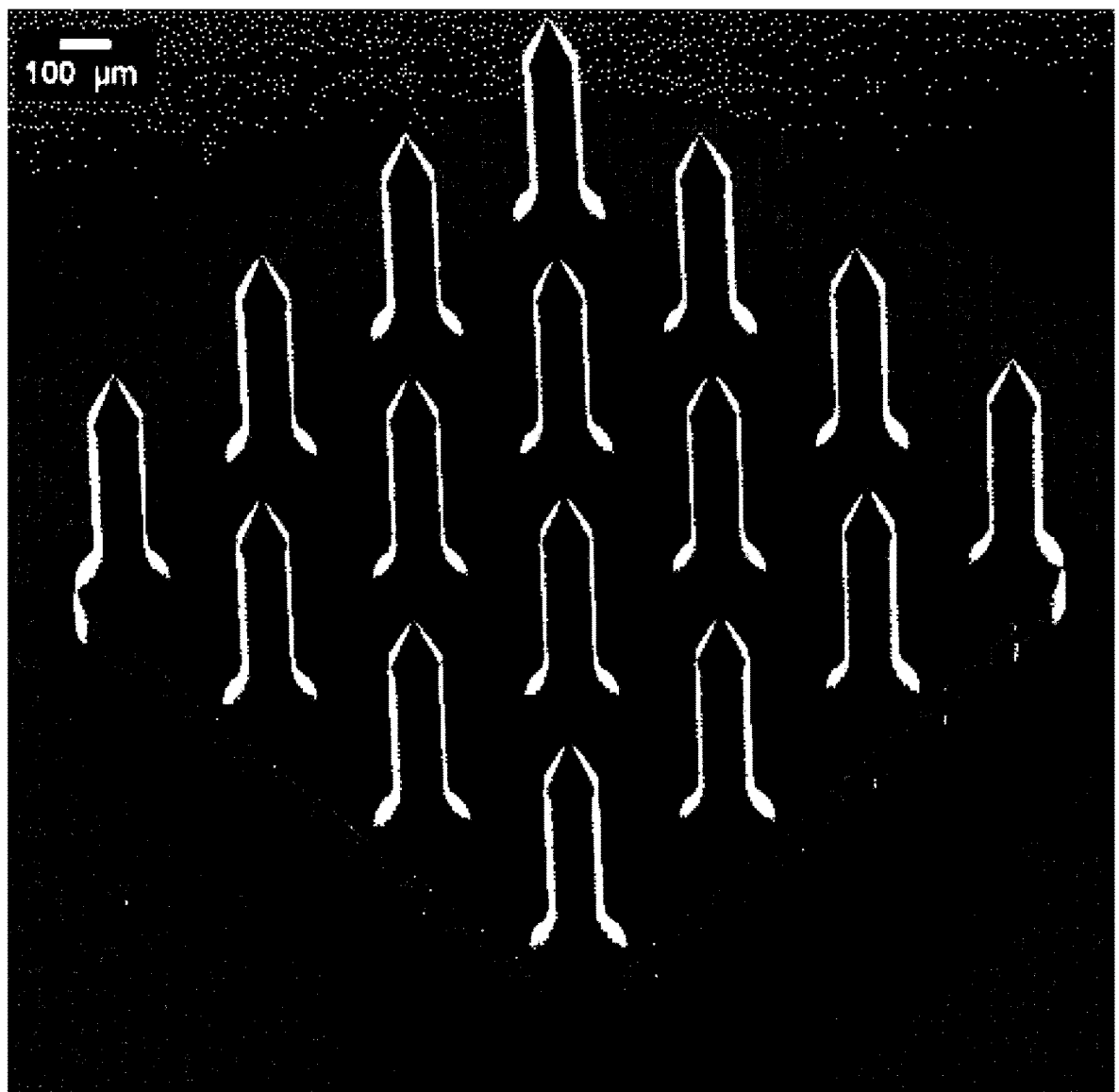
FIG. 19 is a schematic photograph from scanning electron microscope (SEM) for a microneedle array with reservoirs forming a micro-fluidic device.

FIG. 19 is a schematic photograph from scanning electron microscope for a microneedle array with reservoirs forming a micro-fluidic device 1910. The micro-fluidic device of FIG. 19 is also shown and described with respect to FIGS. 9 to 12. The micro-fluidic device 1910 was a prototype design micro/nano-printed from CAD (SolidWorks™) by a two photon polymerization and printing technique of the Photonic Professional GT 3D printing system of Nanoscribe, www.nanoscribe.de. This comparatively recent high speed micro and nano printing system was used with the Dip-in Laser Lithography (DiLL) function as well as other operating parameters and configurations as described elsewhere herein.

A mould of the master die microfluidic device 1910 was cast using a silicone elastomer of PDMS as described elsewhere herein. The negative mould accurately replicated the 500 nm fine features and the larger micro-needle and reservoir features of the of the master die of the 3D printed prototype design, for example as discussed with respect to Carvalho, B., E. Schilling, N. Schmid, and G. Kellogg. "Soft embossing of microfluidic devices. in Proc. 7th Int. Conf. on Miniaturized Chemical and Biochemical Analysis Systems": MicroTAS 2003 (Squaw Valley, Calif., USA, 5-9 Oct. 2003) 2003.

The negative elastomeric mould was used to emboss a thermoplastic material in a novel and improved soft embossing process. Optimal thermoplastics for this application should have a low melt viscosity and have a high affinity for the elastomeric mould. The high affinity may be expressed as a small contact angle between the molten thermoplastic and the PDMS, both being hydrophobic. In other words the molten thermoplastic "wets" the mould readily in a highly mobile surface flow across the mould surface and recesses. Accordingly with such matching between the thermoplastic and the mould surface properties at the embossing temperature very little pressure, if at all, is required for the molten thermoplastic to readily penetrate the finer features of the negative mould. That is, surface flow of the molten thermoplastic may occur into the mould recesses with gravity alone given the appropriate configuration, surface properties and sufficient time.

A suitable thermoplastic material to match PDMS was Zeonor 1060R as described elsewhere herein.

The mould was placed uppermost onto a lowermost stainless steel plate of a press so that the recesses of the mould were facing upwards. One or two small thermoplastic pellets were then loaded onto the mould. The thermoplastic pellets may have approximate dimensions of 2 mm diameter by 4 mm long. Each mould was approximately 20 mm in diameter and may have several microfluidic devices impressed within it. The uppermost stainless steel plate of the press was then brought into touching contact with the pellets, as detected by the computer controlled press. The two stainless steel plates had approximately the same diameter as the mould.

Figure 20:
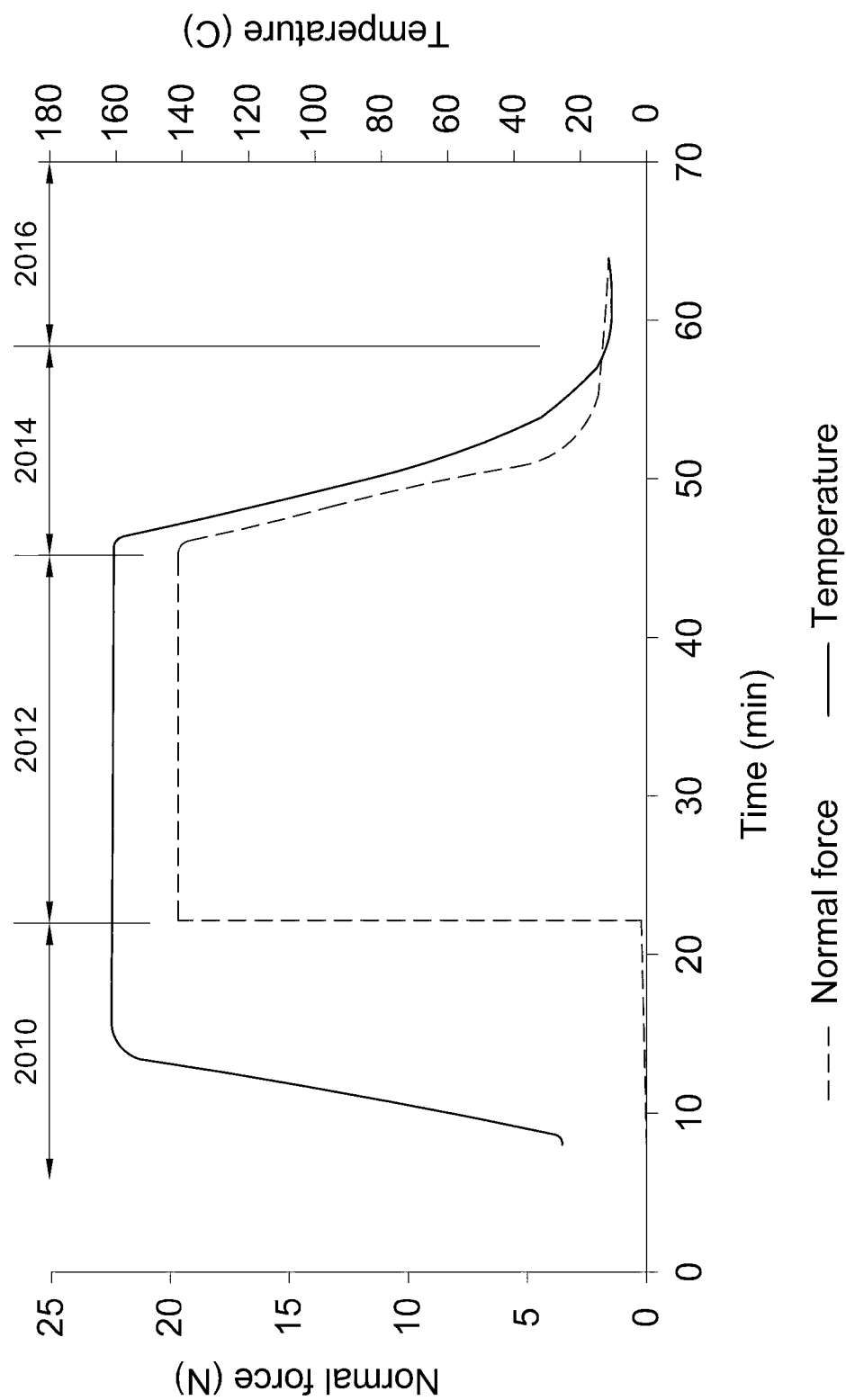
FIG. 20 is a schematic graph showing with time the corresponding temperature in the isothermal chamber and the corresponding compressive/normal force applied for the re-configured press.

The two plates of the press together with the mould and thermoplastic pellets were then encased in an isothermal chamber and heated in a computer controlled fashion as shown in FIG. 20. Atmospheric pressure was used throughout.

FIG. 20 is a schematic graph showing with time the corresponding temperature in the isothermal chamber and the corresponding compressive/normal force applied. An initial period 2010 was to a heating to 160° C. without the application of any significant force to the melting thermoplastic, whilst still maintaining contact between the melting thermoplastic and the upper plate. The sufficient temperature of 160° C. was selected to be in the approximate range of 55° to 65° C. above the glass transition temperature of the thermoplastic (Tg=100° C. for Zeonor). Alternatively the sufficient temperature may be in the approximate range of 30° to 55° C. above the glass transition temperature. This high moulding temperature decreases the viscosity of the molten thermoplastic sufficiently so that it easily flows and penetrates the mould cavities. In addition with the similar surface properties of the thermoplastic and mould both being hydrophobic, capillary tension further aids in completely filling of the mould recesses/cavities at very low applied pressure and without voids or gas inclusions. Accordingly it was not necessary to apply a vacuum to the PDMS mould during embossing because no significant air was trapped in any mould cavities during the embossing process.

Higher temperatures than approximately 160° C. were avoided in order to maintain the integrity of the PDMS mould. In addition higher temperatures were not found to improve the fine feature resolution, as replicated devices had a fine feature limit of approximately 500 nm as dictated by the master die and how the master die was made.

For an embossing run the temperature was maintained closely to the set temperature as detailed below for the press used. Preferably +/−1° C. or more preferably +/−0.1° C. However between embossing runs the temperature may be set in the range of approximately 155° to 165° C. with similar results.

A second period 2012 or compressive phase 2012 was when the upper plate was brought towards the lower plate in a controlled, steady fashion at a constant force of 19.52±0.64 N (mean±standard deviation) for the 20 mm diameter plates. The force range given here is an average across many embossing runs. The force applied for a particular embossing run was typically considerably more constant than the average given here, see below. The compressive period 2012 was begun after a sufficient time for the through heating and melt of the thermoplastic pellets, otherwise damage to the mould may occur and a poor replication result. The compressive period 2012 was continued until shortly before the applied, normal force would become unstable. The instability of the applied compressive force corresponded to the bulk flow of the thermoplastic having progressed to the edges of the plates with a protruding meniscus, the protruding meniscus probably contributing to the inability to maintain a constant compressive force.

Excessive compressive force may deform the PDMS mould and should be avoided. PDMS has a Young modulus of approximately 750 kPa. Accordingly the 20 mm diameter moulds were subjected to a set compressive force of approximately 19 N, corresponding to an approximate set compressive pressure between the two plates of 60 kPa. The pressure of 60 kPa was well below the Young' modulus and any appreciable deformation of the PDMS mould.

Preferably the set compressive pressure was maintained at +/− 1 kPa or more preferably at +/−0.1 kPa. Alternatively the set pressure may be as provided by the computer controlled press as described below.

A third period 2014 was then begun to reduce the temperature and the compressive force approximately simultaneously as shown in FIG. 20.

The mould and the thermoplastic were cooled down further in a fourth period 2016 to approximately 10° to 15° C. which was maintained for 15-20 minutes with constant force (1.6 N) to ensure complete solidification of the thermoplastic in the cooled mould. The solidified thermoplastic micro-needle arrays and associated structures such as the reservoirs were then easily and robustly peeled off the mould without fracture, deformation or defect.

It will be readily appreciated that other solidification agents, other than temperature cycling a thermoplastic, may used for forming the replica microfluidic device. For example the use of UV curing or catalysts for a suitable resin or plastic as described elsewhere herein. In addition the surface flow properties of such alternative resins and plastics may be adjusted to achieve the same effect as described above for the thermoplastic material.

Figure 21:
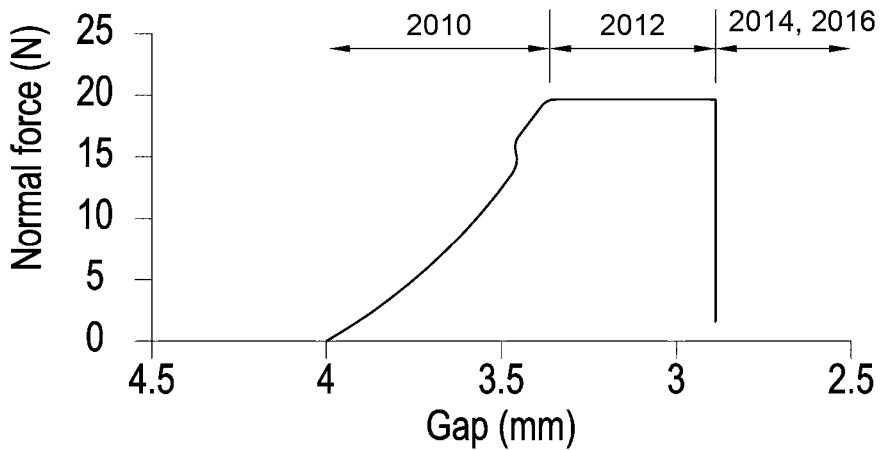
FIGS. 21 to 23 are schematic graphs showing the other process parameters of the new embossing process shown in FIG. 20.
Figure 22:
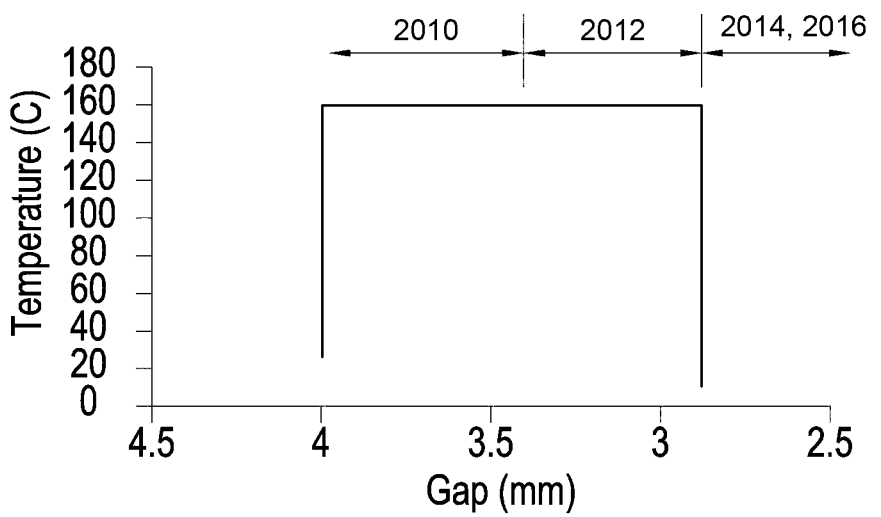
Figure 23:
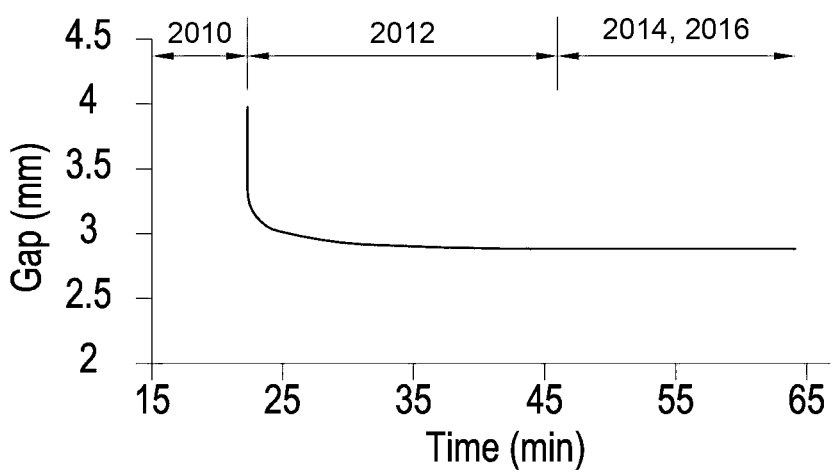

FIGS. 21 to 23 are schematic graphs showing the other process parameters of the new embossing process. The various periods described with respect to FIG. 20 are also shown in FIGS. 21 to 23. FIG. 21 is a graph of the gap between the press plates and the compressive/normal force applied.

FIG. 22 is a graph of the gap between the press plates and the temperature in the isothermal chamber enclosing the two plates, the mould and the thermoplastic material.

FIG. 23 is a graph of the elapsed time and the gap between the two press plates.

Figure 24:
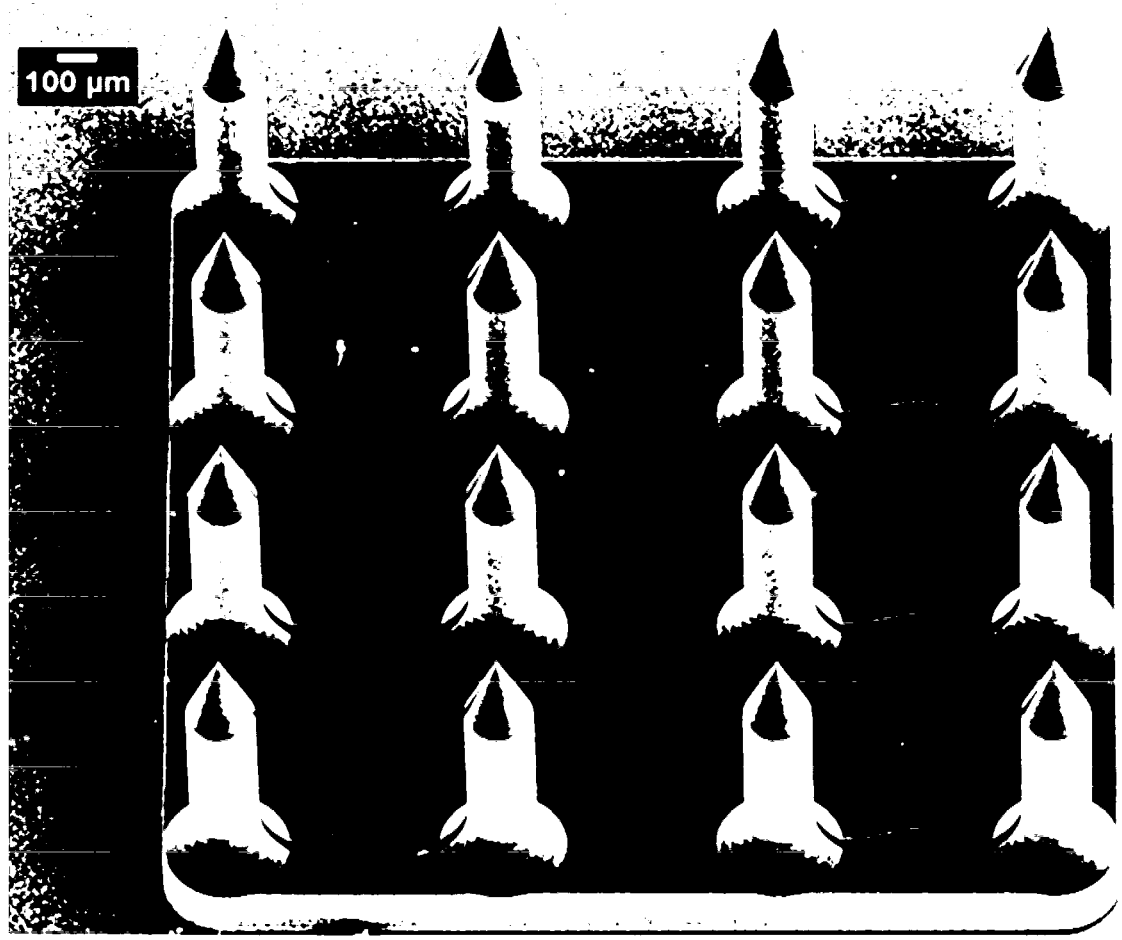
FIG. 24 is a schematic photograph from a SEM of the replicated micro-fluidic device from the master die of FIG. 19, the photograph of the replica microfluidic device of FIG. 24 was taken after it had been inserted into rabbit skin and withdrawn.

FIG. 24 is a schematic photograph from a SEM of the replicated micro-fluidic device from the master die of FIG. 19. The accurate and precise reproduction of all the fine and the large features of the master die of FIG. 19 is clearly apparent in the replica of FIG. 24. In addition, the photograph of the replica microfluidic device of FIG. 24 was taken after it had been inserted into rabbit skin and withdrawn. The integrity and robustness of the replica microfluidic devices is described below.

In order to achieve the steady and highly controlled nature of the temperature and normal force applied by compressing plates, a computer controlled rheometer was adapted for use as a slow, isothermal press. The precision, computer controlled rheometer which was adapted for use was a "Kinexus Pro+" rheometer, manufactured by Malvern Instruments Ltd., Worcestershire, UK, www.malvern.com. Examples of its superior performance characteristics are as follows: normal/compressive force resolution 0.5 mN, normal force response time <10 ms, normal force range 0.001 to 20 N (to 50 N by option) isothermal temperature range −40° C. to 200° C. and temperature resolution 0.01° C. In comparison earlier trials by the inventors with a primitive "Carver" press pressures of approximately twice to three times or more than the above could only be applied and were found to impart defects to the fine featured tip of the micro-needle, probably due to distortion of the mould.

In addition the Kinexus rheometer, when reconfigured as a slow, isothermal press, provided a non-pulsatile compression. That is, the advancing flow of molten thermoplastic proceeded regularly and smoothly across the mould surfaces and recesses. In contrast more primitive press configurations in the prior art are prone to sticking and pulses or jumps in movement at the microscopic level.

In contrast to the elastomeric mould preferably used as above, more rigid molds require taper angles for a master die or form so that de-moulding may occur without damage to the master die and the formed replica. However for the new improved embossing process of the invention a taper angle is not required since the elastomeric mould used deforms around the larger features of the micro-fluidic device during de-moulding.

The PDMS moulds used here by the inventors have been reused over 18 times over a year at least without detectable damage or fouling of the surface or recesses/cavities. In addition the replica micro-devices produced each time have been accurately and precisely reproduced with respect to the master die used to originally form the mould.

It will be readily appreciated that the cycle time of the new and improved embossing process may be shortened, with more rapid heating and cooling cycles. In addition each mould may also carry a higher density of micro-fluidic devices. The example of FIG. 24 was one micro-fluidic device of four on the 20 mm diameter mould. Given the dimensions of the micro-fluidic device shown in the SEM photograph, a considerably higher output of replica devices may be obtained by increasing the density of device impressions in the mould. FIG. 18 describes one technique for up-scaling production by producing many secondary master dies so as to increase the density of devices within a composite mould.

It will also be readily appreciated that the manufacture may be scaled-up by applying and adapting this new embossing process to prior art techniques of stamp embossing, injection molding, and reel-to-reel embossing.

Further micro-needle and micro-fluidic device component geometries were replicated with submicron fidelity. Micro-needle length ranges from approximately 650 to 1000 µm; with shaft diameters of 150 µm and 30 µm (radius or depth) open side-channels were replicated. Micro-fluidic devices with an array of micro-needles approximately spaced at 600 micrometres were also replicated faithfully down to the 500 nm feature limit of the master die. In the following FIGURES further examples of micro-fluidic device component replications are provided.

Figure 25:
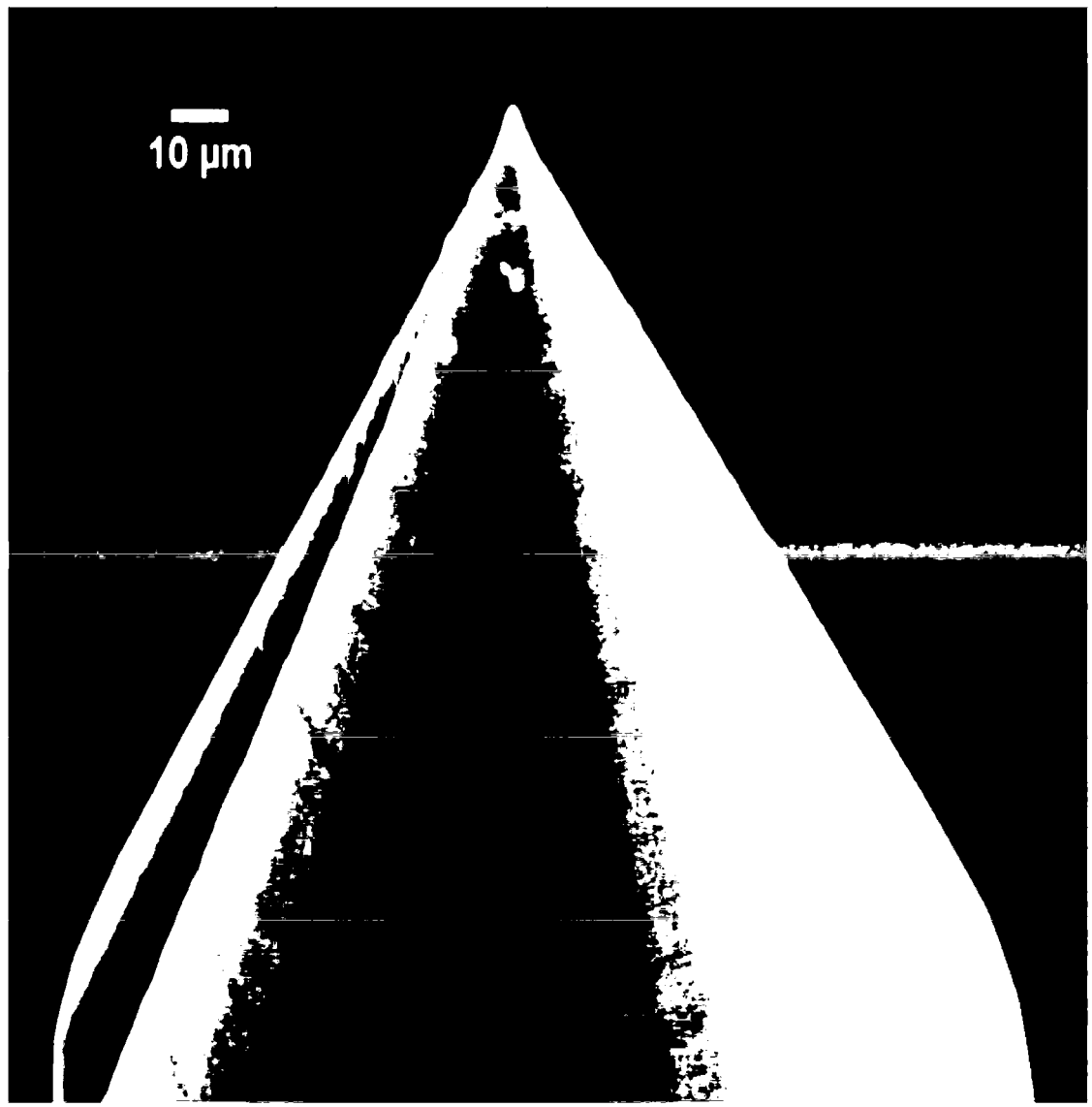
FIG. 25 is a schematic photograph from a SEM of an ultra-sharp, replicated micro-needle tip.

FIG. 25 is a schematic photograph from a SEM of an ultra-sharp, replicated micro-needle tip. The ultra-sharp tip has an approximate radius of curvature of 500 nm, corresponding to the printing resolution used to produce the master die.

Figure 26:
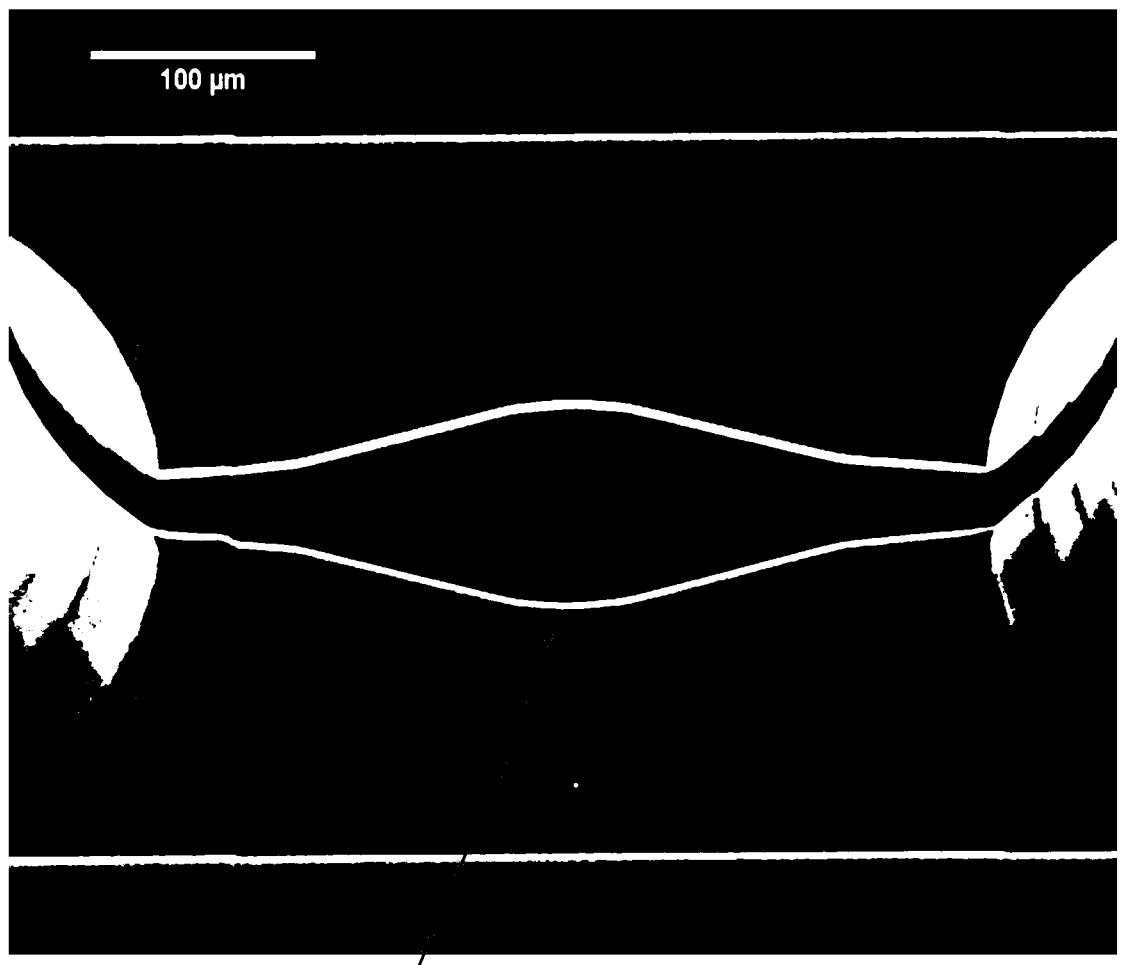
FIG. 26 is a schematic photograph from a SEM of a one micrometre peripheral lip about a reservoir of a replicated micro-fluidic device.

FIG. 26 is a schematic photograph from a SEM of a one micrometre peripheral lip 2610 about a reservoir of a replicated micro-fluidic device.

Figure 27:
FIG. 27 is a series of three schematic photographs from a SEM of replica conical micro-needles with a reservoir at the base of each conical micro-needle.

FIG. 27 is a series of three schematic photographs from a SEM of replica conical micro-needles with a reservoir at the base of each conical micro-needle. An open channel is also shown along the side of each micro-needle, extending from the ultra-sharp tip to the reservoir at the base of the micro-needle.

A microblade with multiple channels and reservoirs is described below with respect to FIGS. 32 to 35.

Hollow micro-needles (not shown) were also replicated. The hollow, replica micro-needles had a height of approximately 600 micrometres, a bore or a lumen diameter of approximately 30 micrometres and an approximate depth of 600 micrometres. Accordingly the bore depth to diameter aspect ratio was approximately at least 20:1 that may be replicated by the new embossing technique.

The replicated thermoplastic micro-needles were mechanically tested and found to be robust with a yield or a failure strength of greater than 1 N per micro-needle for a downward force upon the micro-needle. A one Newton force per micro-needle is considerably higher than the penetration or insertion force required for the skin with such micro-needles. In addition FIG. 24 shows a replica micro-needle array after insertion into a rabbit ear. The array of micro-needles are intact after use and are not deformed or fractured.

The micro-needles replicated here with a thermoplastic such as Zeonor were also noted to fail by deformation in a folding over manner. Prior art micro-needles of more brittle materials are prone to fracture with consequent shedding of foreign material into the dermis.

Figure 29:
FIGS. 28 and 29 are schematic photographs from an optical microscope showing an uptake of an aqueous fluid with green dye being taken up by the tip of a replicated micro-needle and then transferred into a reservoir at the base of the micro-needle shown.
Figure 28:

FIGS. 28 and 29 are schematic photographs from an optical microscope showing an uptake of an aqueous fluid with green dye being taken up by the tip of a replicated micro-needle and then transferred into a reservoir at the base of the micro-needle shown. The replicated micro-needle was surface treated so as to be hydrophilic. FIG. 28 shows the unfilled reservoir 2810. FIG. 29 shows the filled reservoir 2910. It is clear that the micro-needles replicated here may readily collect fluids into a reservoir.

Figure 30:
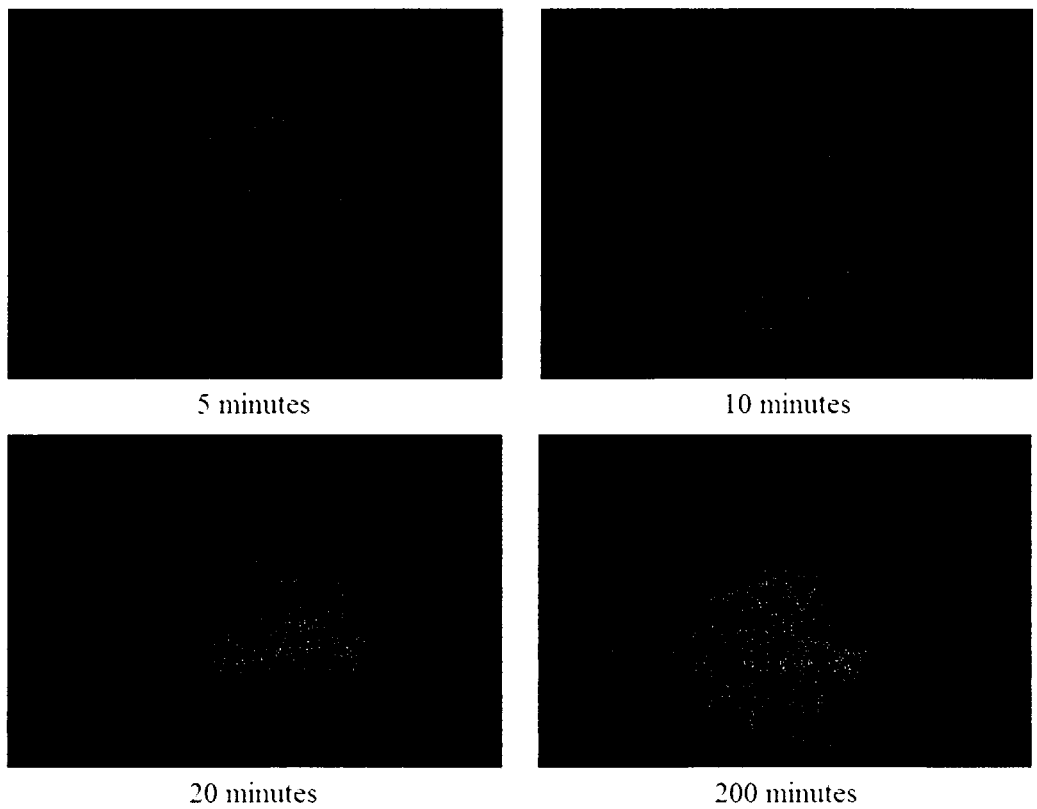
FIG. 30 is a time series of four confocal microscopy images showing a diffusion of a fluorescein solution, delivered by the replicated microfluidic device of FIG. 24, into a subcutaneous tissue of a rabbit ear.

FIG. 30 is a time series of four confocal microscopy images showing a diffusion of a fluorescein solution into a subcutaneous tissue of a rabbit ear. The replicated micro-fluidic device of FIG. 24 was used to deliver a fluorescein solution from the multiple reservoirs into the subcutaneous tissue of a rabbit ear. At five minutes the puncture points within the skin of the micro-needle array and the immediate, circular distribution of the fluorescein hydrophilic tracer solution about each micro-needle are clearly seen. After 20 minutes the puncture points into the skin are no longer visible and the fluorescein tracer has distributed throughout the array injection site and beyond. FIG. 30 demonstrates that the replicated micro-needle array readily punctures the skin to the required depth, the reservoirs with open channels deliver a fluorescein tracer below the outer layers of the skin so that fluorescein tracer may diffuse into the bodily fluids below the outer layers of the skin. In addition the very small diameter of the replicated micro-needles allows for the skin to recover its integrity quickly from the injection. Accordingly replicated micro-fluidic devices of the invention may be readily used to deliver medicaments/drugs and the like to the skin and bodily fluids associated with the skin.

The replicated micro-fluidic device used for FIG. 30 was applied using a modified spring-loaded pen to propel with sufficient velocity the micro-needle array against the skin to penetrate to substantially the full length of the micro-needles. The superior and new embossing technique for replicating the exceptionally sharp and smooth master die micro-needles allows for easy application of the micro-fluidic device to the rabbit ear and consequent recovery of the device after use.

FIG. 24 shows the replicated micro-fluidic device used in FIG. 30, after removal from the rabbit's ear. No damage was apparent to the device of FIG. 24, as described elsewhere herein.

A micro-fluidic device may be designed to undertake glucose assays as follows. The glucose micro-fluidic assay device may include filling of the channel and/or reservoir network with a gel that contains reagents for measuring an analyte such as glucose in bodily fluids. The gel in the channels may extend up the micro-needle.

The gel may retain enzymes required for detection of the analyte (e.g., glucose oxidase to produce hydrogen peroxide) which can be measured by an electrochemical sensor or a fluorogenic assay (e.g., horse radish peroxidase, Amplex Red assay, etc.). In addition chemoluminescence (e.g., luminol) or electrochemoluminescence may be used for their enhanced sensitivity and real time application. For example, a real time lactate sensor may use electrochemoluminescence for pulsed measurements.

The gel may exclude interfering substances or cells, but may allow the rapid diffusion of the analyte from the bodily fluids, in this case glucose (or alternatively lactate), into the gel of the micro-needle well or reservoir.

Figure 31:
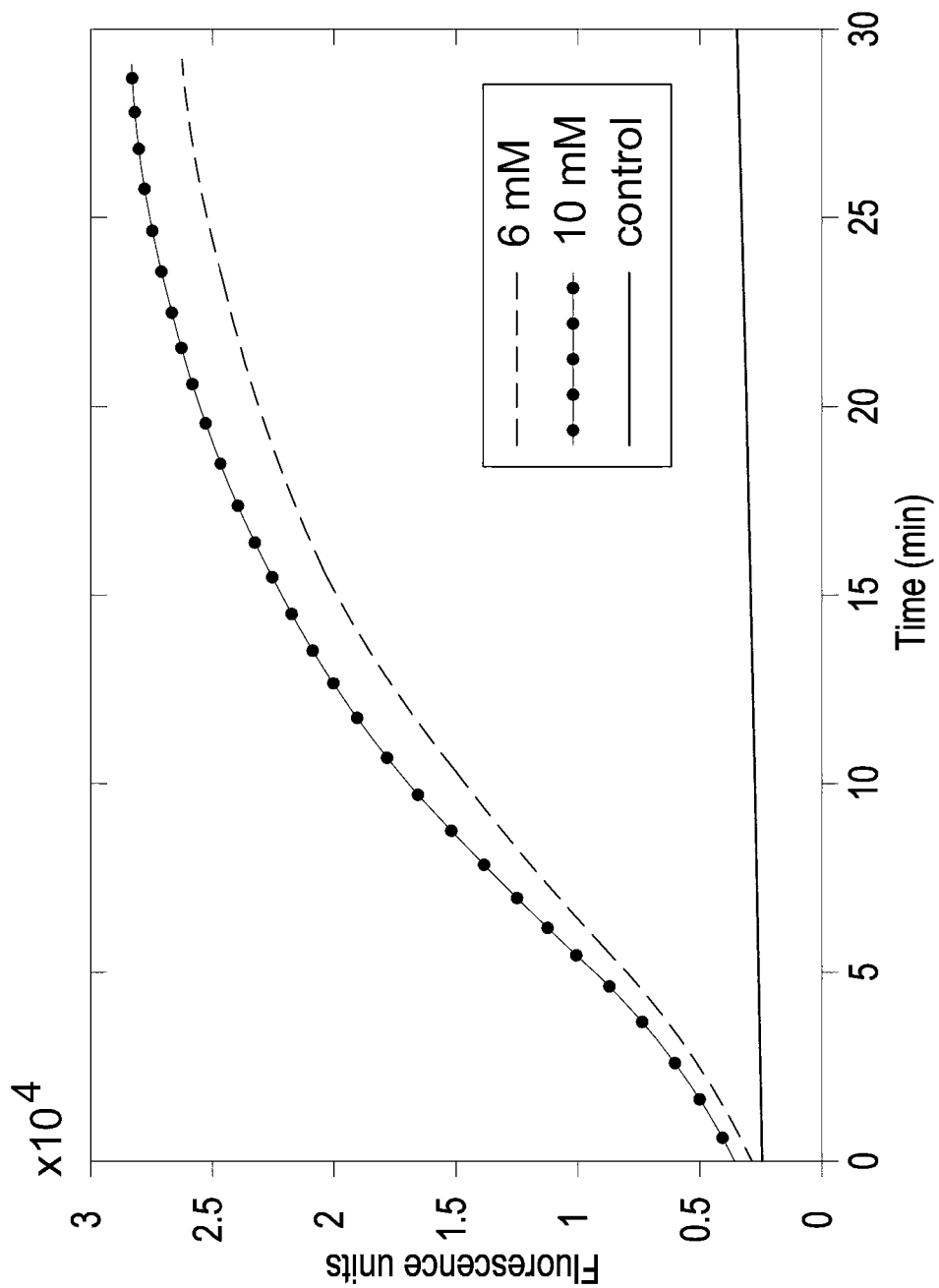
FIG. 31 is a schematic of a graph quantifying a glucose analyte in nanolitre volumes for a proposed glucose assay with a microfluidic device.

FIG. 31 is a graph quantifying a glucose analyte in nanolitre volumes as an indication to the required sensitivity to quantify glucose in a nanolitre of fluid using a photoreceptor detector. In this case a fluorescent microscope was used as the photoreceptor detector.

Figure 32:
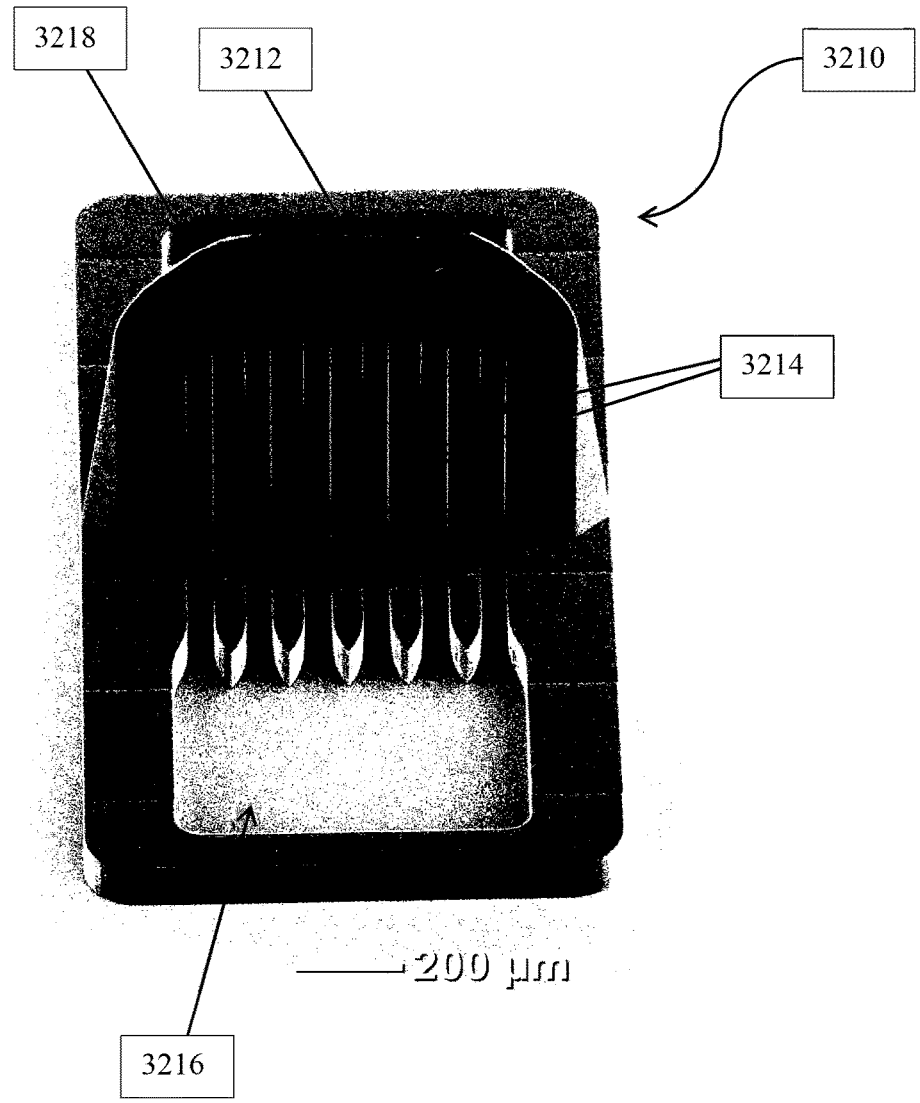
FIG. 32 is a schematic of a SEM photograph of a microblade 3210 microfluidic device.

FIG. 32 is a schematic of a SEM photograph of a microblade 3210 microfluidic device. The master die microblade 3210 of FIG. 32 features a sharp, upright blade 3212. Extending downwards from the blade 3212 are multiple open channels 3214. The open channels 3214 extend into respective front and rear reservoirs 3216, 3218 with respect to the upright blade 3212. The microblade may be used to pierce the skin and draw bodily fluids. A height and a width of the blade are approximately 800 and 1000 micrometres, respectively and as per FIGS. 33 and 34. The reservoir 3216, 3218 volume is approximately 20 nl.

An advantage of this microblade design of a microfluidic device is that the blade 3212 and multiple channels 3214 may be more likely to section or puncture a capillary compared with a micro-needle array. In addition the multiple larger channels may draw larger volumes of capillary blood and other bodily fluids than a micro-needle array. A patch may be fabricated that contains an array of replicated microblades, as described herein for the microneedles.

Figure 33:
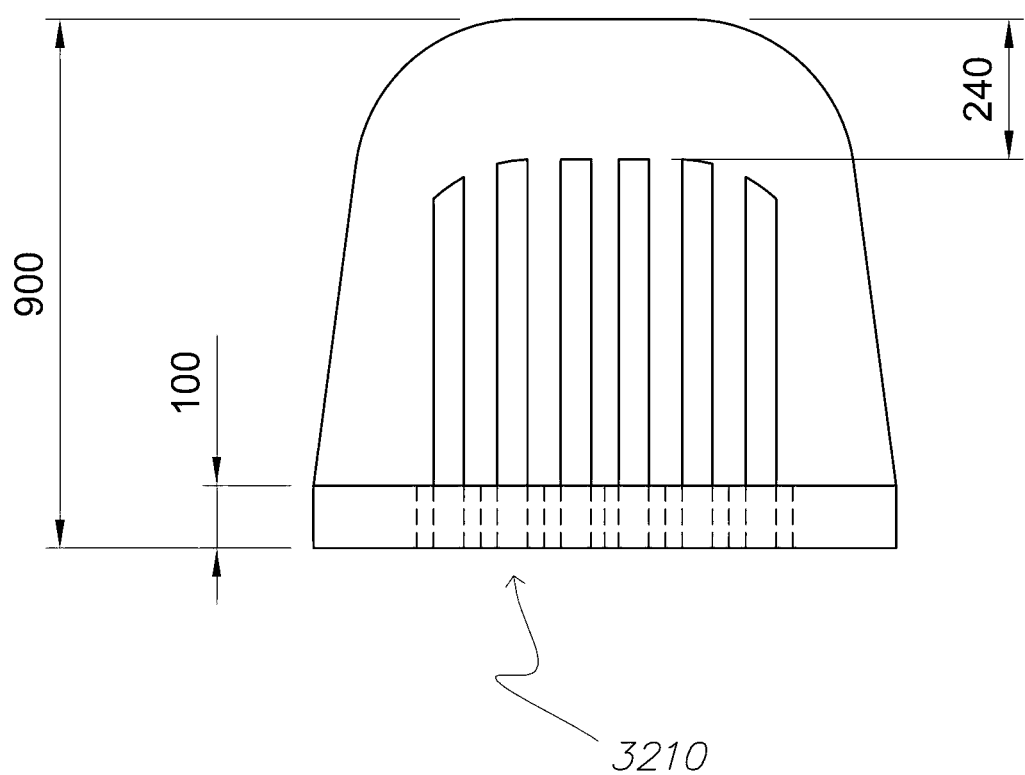
FIGS. 33 to 35 are a schematic of respective front elevational, plan and perspective views from a CAD drawing of the microblade of FIG. 32.

FIG. 33 is a schematic of a front elevational view from a CAD drawing of the microblade 3212. FIG. 33 also shows the approximate dimensions of the microblade master die that was nano- and micro-printed.

Figure 34:
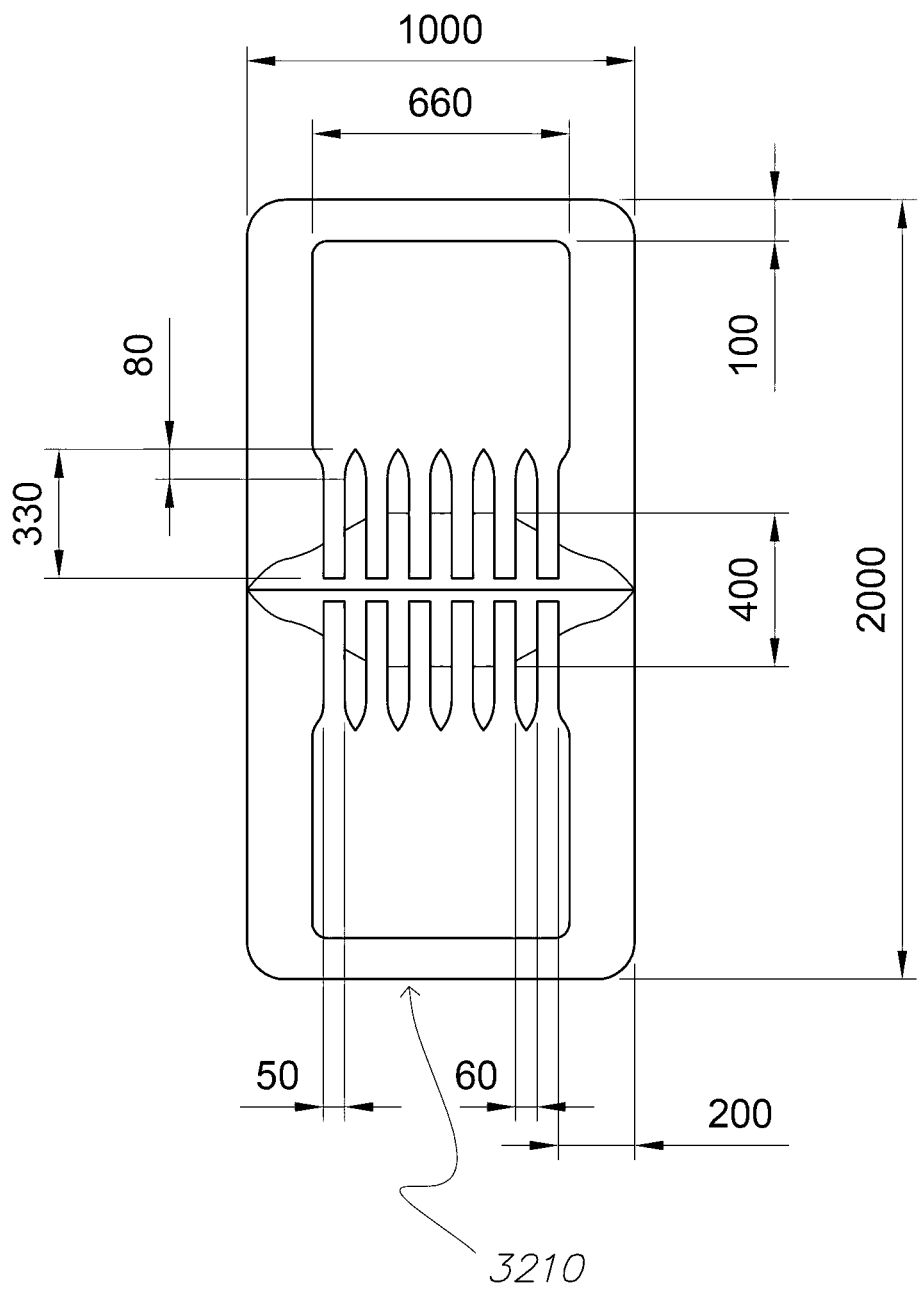

FIG. 34 is a schematic of a plan view from a CAD drawing of the microblade 3212. FIG. 34 also shows the approximate dimensions of the microblade master die.

Figure 35:
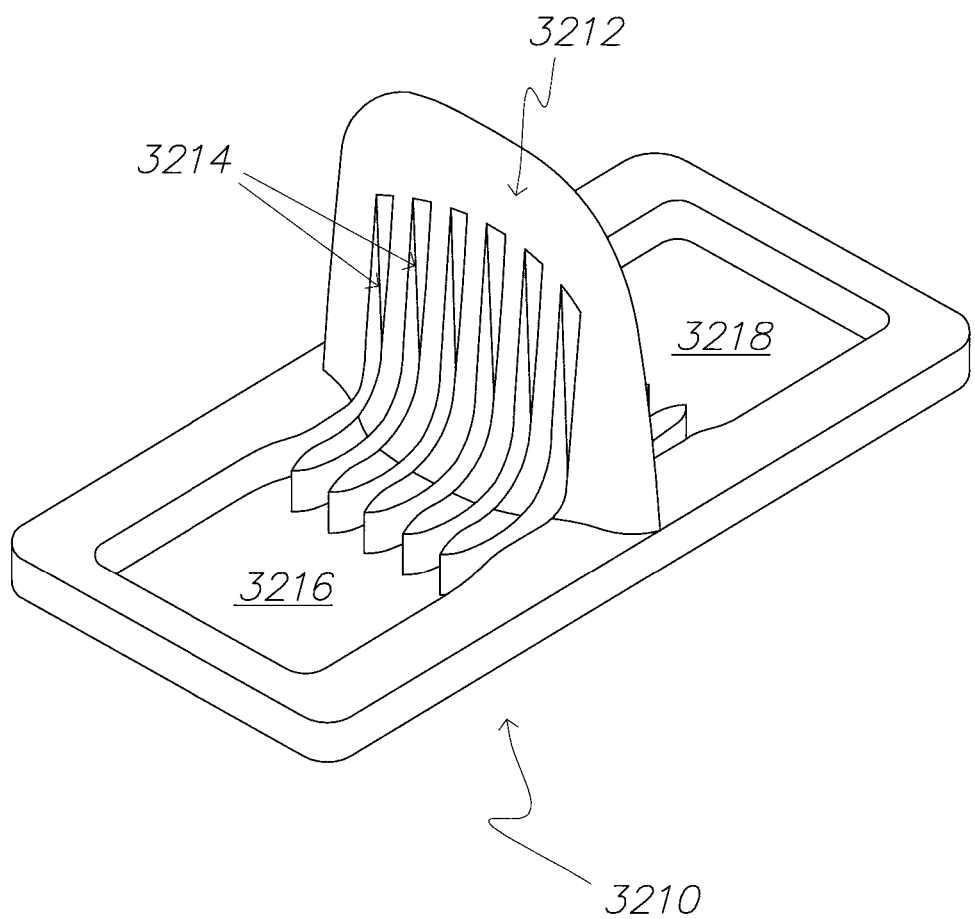

FIG. 35 is a schematic of a perspective view from a CAD drawing of the microblade 3212.

It will be readily appreciated that the microblade microfluidic device of FIGS. 32 to 35 and other microfluidic device designs may be readily replicated in a mass production as described herein.

In this specification, terms denoting direction, such as vertical, up, down, left, right etc. or rotation, should be taken to refer to the directions or rotations relative to the corresponding drawing rather than to absolute directions or rotations unless the context require otherwise.

Although the invention has been herein shown and described in what is conceived to be the most practical and preferred embodiments, it is recognized that departures can be made within the scope of the invention, which are not to be limited to the details described herein but are to be accorded the full scope of the appended claims so as to embrace any and all equivalent assemblies, devices, apparatus, articles, compositions, methods, processes and techniques.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

The invention claimed is:

1. A replica microfluidic device including:
a plurality of micro-needles across a support member;
at least one reservoir in the support member; and
a channel providing fluid communication between at least one of the plurality of micro-needles and the at least one reservoir,
wherein a first aspect ratio of a height of each of the plurality of micro-needles to a radius of curvature of a tip of each of the plurality of micro-needles is approximately 1400:1.

2. A device according to claim 1, wherein a second aspect ratio of a depth of the at least one reservoir to a width of the at least one reservoir is approximately 5:1.

3. A device according to claim 1, wherein a third aspect ratio of a length of the channel to a depth of the channel is approximately 20:1.

4. A device according to claim 1, wherein each of the plurality of micro-needles has a fine feature resolution of less than 500 nanometres.

5. A device according to claim 1, wherein the height of each of the plurality of micro-needles is in the range of approximately 650 to 1000 micro-metres.

6. A device according to claim 1, wherein a depth of the at least one reservoir is at least 100 micro-metres.

7. A device according to claim 1, wherein a depth of the channel is in the range of approximately 20 to 100 micrometres.

8. A device according to claim 1, wherein each of the plurality of micro-needles has a yield strength of at least approximately one Newton.

9. A device according to claim 1, wherein a surface of the at least one reservoir and the channel are hydrophilic.

10. A device according to claim 1, wherein the support member includes a surface across which the plurality of micro-needles is disposed, and wherein the surface of the support member is hydrophobic.

11. A microneedle for communicating fluids, the microneedle comprising:
a body having at a first end a pointed tip to penetrate an epidermal layer;
a base at an opposing second end of the body; and
an open channel extending along a side of the body from the first end to the second end,
wherein the channel is configured to communicate fluids between the tip and the base of the microneedle, and
wherein a first aspect ratio of a height the microneedle to a radius of curvature of a tip of the micro-needle is approximately 1400:1.

12. A patch comprising an array of microneedles according to claim 11, wherein the array of microneedles are supported on a support member.

13. A patch according to claim 12, wherein a plurality of open channels extend into the support member to form a channel network in communication with at least one reservoir.

14. A patch according to claim 13, wherein the channel network is pre-treated to react to a presence of a predetermined substance within a bodily fluid.

15. A patch according to claim 14, wherein the pre-treatment is a gel containing at least one reagent for an analyte detection.

16. A method of manufacturing a replica micro-needle for communicating fluids according to claim 11, the method comprising the steps of:
  casting a mould in a resilient material from a master die of a microneedle, the die having a microneedle body having at a first end a pointed tip to penetrate an epidermal layer, a base at an opposing second end of the body, and an open channel extending along a side of the body from the first end to the second end;
  moulding a warm thermoplastic into the mould to form the replica microneedle; and
  separating the moulded replica microneedle from the mould.

* * * * *